(12) United States Patent
Adriano

(10) Patent No.: US 7,069,665 B1
(45) Date of Patent: Jul. 4, 2006

(54) CORRECTING FOOT ALIGNMENT

(75) Inventor: Rosa Adriano, Caledonia, MI (US)

(73) Assignee: Biocorrect L.L.C., Kentwood, MI (US)

(*) Notice: Subject to any disclaimer, the term of this patent is extended or adjusted under 35 U.S.C. 154(b) by 0 days.

(21) Appl. No.: 10/604,418

(22) Filed: Jul. 18, 2003

Related U.S. Application Data

(60) Provisional application No. 60/397,446, filed on Jul. 19, 2002.

(51) Int. Cl.
*A61B 5/103* (2006.01)

(52) U.S. Cl. .............................. 33/515; 33/512; 33/562; 33/3 R; 36/43

(58) Field of Classification Search .......... 33/512–513, 33/515, 3 R, 4–6, 562; 36/43, 140, 145, 36/173
See application file for complete search history.

(56) References Cited

U.S. PATENT DOCUMENTS

| | | | | |
|---|---|---|---|---|
| 3,358,373 | A * | 12/1967 | Martin | 33/512 |
| 4,084,333 | A * | 4/1978 | Del Vecchio | 36/43 |
| 4,108,164 | A * | 8/1978 | Hall, Sr. | 33/512 |
| 4,170,233 | A | 10/1979 | Bunsick | |
| 4,434,792 | A * | 3/1984 | Rosenberg | 602/24 |
| 4,522,777 | A | 6/1985 | Peterson | |
| 4,530,173 | A | 7/1985 | Jesinsky, Jr. | |
| 4,662,079 | A * | 5/1987 | Graf et al. | 33/512 |
| 4,759,357 | A * | 7/1988 | Allart et al. | 36/140 |
| 4,771,548 | A * | 9/1988 | Donnery | 33/512 |
| 4,802,494 | A | 2/1989 | Gardiner | |
| 5,025,476 | A * | 6/1991 | Gould et al. | 33/3 B |
| 5,431,624 | A * | 7/1995 | Saxton et al. | 36/89 |
| 5,746,011 | A * | 5/1998 | Hedstrom | 36/44 |
| 5,790,256 | A * | 8/1998 | Brown et al. | 33/515 |
| 5,822,873 | A * | 10/1998 | Meilman | 33/365 |
| 5,826,351 | A * | 10/1998 | Tsuji | 36/31 |
| 5,873,172 | A * | 2/1999 | Siemel | 33/512 |
| 5,979,067 | A * | 11/1999 | Waters | 33/512 |
| 6,105,283 | A | 8/2000 | Park | |
| 6,163,971 | A * | 12/2000 | Humphries et al. | 33/515 |
| 6,219,929 | B1 * | 4/2001 | Tasker et al. | 33/515 |
| 6,293,026 | B1 * | 9/2001 | Lee et al. | 33/512 |
| 6,361,506 | B1 * | 3/2002 | Saenger et al. | 33/512 |
| 6,594,922 | B1 * | 7/2003 | Mansfield et al. | 36/145 |
| 2002/0100179 | A1 * | 8/2002 | Root | 33/515 |
| 2003/0005599 | A1 * | 1/2003 | Panaccione | 36/43 |
| 2004/0168329 | A1 * | 9/2004 | Ishimaru | 33/3 R |
| 2004/0193075 | A1 * | 9/2004 | Martindale | 33/515 |

* cited by examiner

*Primary Examiner*—Yaritza Guadalupe
(74) *Attorney, Agent, or Firm*—McGarry Bair PC

(57) ABSTRACT

A component system of footwear corrective alignment insoles provides adjustment of the alignment of a human foot based upon evaluation and measurement of structural anomalies in the foot. A subtalar joint goniometer measures the angular alignment of the foot with a patient's leg properly inclined with respect thereto. A database contains data with selected relationships between the degree of a patient's foot pronation and supination and a variety of corrective pads for use with an insole for correcting pronation and supination. The foot pronation and supination is corrected by first measuring a patient's foot pronation and supination, comparing the measured pronation or supination with a database that correlates degrees of pronation and supination with a variety of corrective pads for use with a corrective alignment insole, selecting corrective pads from the database that correspond to the measured pronation or supination, and mounting the selected corrective pads to a base insole.

57 Claims, 19 Drawing Sheets

DATABASE CHART

| Subtalar Joint Goniometer Measurement | Shoe Type | Corrective Alignment Insole Components |
|---|---|---|
| -5° to 3° (Over-Supination) | • Cushion<br>• Flexible Forefoot<br>• Curved | Base Insole + Supination Control Pad + Supplementary Supination Control Pad (Type A) |
| 3° to 6° (Mild Supination) | • Cushion<br>• Flexible Forefoot<br>• Semi-Curved<br>• Light Heel Stability | Base Insole + Supination Control Pad (Type B) |
| 6° to 9° (Neutral) | • Cushion/Stability<br>• Semi-Curved<br>• Heel Stability | Base Insole (Type C) |
| 9° to 12° (Mild Pronation) | • Full Stability<br>• Semi-Straight | Base Insole + Supplementary Motion Control Pad (Type D) |
| 12° to 15° (Over-Pronation) | • Motion Control<br>• Straight | Base Insole + Motion Control Pad (Type E) |
| >15° (Over-Pronation) | • Motion Control<br>• Straight | Base Insole + Motion Control Pad + Supplementary Motion Control Pad (Type F) |

Fig. 21

FOOT/LEG SYMPTOMATIC CHART

| Symptoms | Corrective Alignment Insole Type | Additional Evaluations |
| --- | --- | --- |
| Achilles Tendonitis | A or B | Leg Length Discrepancy |
| Plantar Fasciitis | C, D, E or F + Increase Arch Support 5° - 6° | |
| First Toe Joint Pain | D, E or F + Arch Support | Bunion and Leg Length Discrepancy |
| Medial Shin Pain | E or F + Arch Support | |
| Lateral Shin Pain | A or B | |
| ITB Pain | D, E or F + Arch Support | |
| Chondromalacia | A, B, E or F | Valgus and Varus Knee |
| Hamstring Pain | A, B, E or F | Piriformis Tightness |
| Painful Gastroc | A, B, E or F | Leg Length Discrepancy |
| Hip pain | A, B, E or F | Leg Length Discrepancy |
| Sciatica | E or F | Leg Length Discrepancy |
| Low Back Pain | E or F | Leg Length Discrepancy |
| Metatarsal Pain | A - F | Leg Length Discrepancy |

Fig. 22

CORRECTING FOOT ALIGNMENT

CROSS REFERENCE TO RELATED APPLICATIONS

This application claims the benefit of U.S. Provisional Application Ser. No. 60/397,446, filed on Jul. 19, 2002.

BACKGROUND OF INVENTION

1. Field of the Invention

The invention relates to correcting foot alignment. In one aspect, the invention relates to an apparatus for measuring the alignment of the human foot. In another of its aspects, the invention relates to a footwear corrective alignment insole kit for correcting foot alignment during standing, walking, or running. In another aspect, the invention relates to measuring instruments for determining the type and amount of corrective alignment required for a foot. In another aspect, the invention relates to a method for correcting the alignment of the human foot.

2. Description of the Related Art

No two human feet are the same. Indeed, an individual's two feet may have vastly different structural characteristics. For example, a person may have low arches, commonly referred to as "flat feet" or "fallen arches." Or, a person may suffer from pronation, i.e. the tendency of the foot to roll inward during walking or running. An individual with flexible ankles may suffer from painful pressure points that develop during walking or running due to the inability of the foot to maintain proper stability and alignment.

Different approaches are taken to correcting problems with foot alignment and structure. Exercises for strengthening the foot and/or ankles can be performed. However, these may be inadequate to correct structural problems such as a low arch. Alternatively, footwear corrective alignment insoles can be used to attempt to compensate for alignment and structural problems, particularly for raising and supporting a fallen arch. Or a corrective alignment insole can be used to stabilize the heel to prevent side-to-side movement of the foot. Frequently, corrective alignment insoles are inadequate to stabilize the foot during the full range of motion experienced during walking or running. Additionally, corrective alignment insoles are generally located underneath the arch and heel portion of the foot, and do not extend beneath the plantar region of the foot and the toes. Consequently, as the foot rolls forward, weight is transferred off the corrective alignment insole which can affect the correction of the foot movement, even exacerbating the problems that the corrective alignment insole is intended to correct.

SUMMARY OF INVENTION

In a first embodiment of the invention, a method of making a shoe correction for the alignment of a person's foot, comprises the steps of, while the person is standing on the foot, inclining the person's lower leg forwardly about the foot a preselected angle from the vertical, and, while maintaining the person's lower leg in the forward inclined position at the preselected angle, measuring the lateral angular alignment of the foot. The method can further comprise the step of selecting from a database appropriate corrective components for incorporation into a shoe to correct the alignment of the person's foot, wherein the database has a correlation between a range of lateral angular alignment values and appropriate corrective components.

The corrective components can include combinations of corrective alignment insole components, including supination, pronation, and arch control pads. The method can further comprise the step of constructing a corrective alignment insole from a base insole and the selected supination, pronation, and arch control pads.

The database can further include a correlation between lateral angular alignment values and an appropriate shoe type, and can further comprise the step of incorporating the corrective alignment insole into the selected shoe type.

The measuring step can be carried out with the aid of a subtalar joint goniometer. The measuring step can include the step of inscribing a reference line along the Achilles' tendon portion of the person's foot, and measuring the lateral angular alignment of the reference line. The method can further comprise the step of constructing a corrective alignment shoe by incorporating into the shoe the selected corrective components.

In an alternate embodiment, a method of making a shoe correction for the alignment of a person's foot can comprise the steps of measuring the lateral angular alignment of the person's foot with respect to a lower portion of the leg, and selecting from a database appropriate corrective components for incorporation into a shoe to correct the alignment of the person's foot.

In yet another embodiment, a kit for quantifying and making a shoe correction for a misalignment of a person's foot comprises a dorsiflexion template adapted to position the person's lower leg at a preselected forward angle with respect to an upper surface of the person's foot adjacent the ankle when the person is standing on the foot, and a subtalar joint inclinometer to measure the lateral angular alignment of the person's foot when the person's lower leg is inclined at the preselected angle. The kit can further comprise at least one corrective alignment insole component comprising a base insole in the general shape of a person's footprint having a lateral portion, a medial portion, and an arch stability portion, at least one supination control pad for adjusting the supination alignment of the person's foot, at least one pronation control pad for adjusting the pronation alignment of the person's foot, and at least one arch control pad for adjusting the support of the person's arch.

The kit can further comprise a database which correlates a range of lateral angular alignment values combinations with at least one of the corrective alignment insole components, wherein the at least one of the corrective alignment insole components can be selected from the database based upon the lateral angular alignment measurement obtained from the subtalar joint inclinometer.

The subtalar joint inclinometer can comprise a subtalar joint goniometer comprising a base portion having an indicator arrow extending orthogonally upwardly therefrom and an alignment portion pivotally attached to the base portion having a protractor scale inscribed thereon. The subtalar joint inclinometer can also comprise a calcaneal bisection gauge comprising a pair of arcuate wings pivotably connected by a hinge to locate the mid-line of the person's heel, and an angle finder to measure the inclination of the mid-line.

In another embodiment of the invention, a corrective alignment insole assembly for making a shoe correction for the alignment of a person's foot comprises a base insole in the general shape of a person's footprint having a lateral portion, a medial portion, and an arch stability portion, and adapted for correcting both pronation and supination in combination with at least one of at least one supination control pad, at least one pronation control pad, or at least one arch control pad, at least one supination control pad for adjusting the supination alignment of the person's foot at least one pronation control pad for adjusting the pronation alignment of the person's foot, and at least one arch control pad for adjusting the support of the person's arch, wherein the at least one supination control pad, the at least one pronation control pad, and the at least one arch control pad are selected based upon a lateral angular alignment measurement of the person's foot.

The base insole can be divided into an irregularly-shaped supination control portion extending along the lateral portion of the base insole, an irregularly-shaped motion control portion extending along the medial portion of the base insole, and a crescent-shaped arch stability portion extending along the arch portion of the base insole.

The at least one supination control pad can comprise an irregularly-shaped member having a variable wedge-shaped cross section corresponding in size and shape to the supination control portion of the base insole, and having an anterior end, a posterior end, a medial edge, and a lateral edge, wherein the thickness of the at least one supination control pad decreases from the lateral edge to the medial edge, and from a portion along the lateral edge to the anterior end and the posterior end. The at least one supination control pad can range in thickness from a maximum of $3/16$ inch at the center lateral edge to $1/16$ inch at the posterior end, to zero inches at the anterior end and along the medial edge. The at least one supination control pad can further comprise an irregularly-shaped central portion.

A supplementary supination control pad can comprise an irregularly-shaped member having a generally wedge-shaped cross section corresponding in size and shape to the supplementary supination control pad portion, attached to the supination control pad at a central portion thereof the supplementary supination control pad portion for increasing the maximum thickness of the supination control pad at its center lateral portion, and having an anterior end, a posterior end, a medial edge, and a lateral edge, wherein the thickness of the supination control pad decreases from the lateral edge to the medial edge, and from a portion along the lateral edge to the anterior end and the posterior end. The supplementary supination control pad can vary in thickness from a maximum of $1/8$ inch at the center lateral edge to zero inches at the anterior end, the posterior end, and the medial edge.

The at least one motion control pad can comprise an irregularly-shaped elongated member having a variable wedge-shaped cross section corresponding in size and shape to the motion control portion of the base insole, and having an anterior end, a posterior end, a medial edge, and a lateral edge, wherein the thickness of the at least one motion control pad decreases from the medial edge to the lateral edge, and from the portion along the medial edge to the anterior end and the posterior end. The at least one motion control pad can range in thickness from a maximum of $3/16$-inch along the anterior portion of the medial edge, to $1/8$-inch at the posterior end, to zero inches at the anterior end and along the lateral edge.

The at least one motion control pad can comprise an irregularly-shaped supplementary motion control pad portion located at the anterior medial portion of the at least one motion control pad. The supplementary motion control pad can comprise an irregularly-shaped member having a generally wedge-shaped cross-section corresponding in size and shape to the supplementary motion control pad portion, attached to the motion control pad at the supplementary motion control pad portion for increasing the maximum thickness of the motion control pad at its anterior medial portion, and having an anterior end, a posterior end, a medial edge, and a lateral edge, wherein the thickness of the at least one supplementary motion control pad decreases from the center medial edge to the anterior end, the posterior end, and the lateral edge. The supplementary motion control pad can vary in thickness from a maximum of $1/8$ inch at the center medial edge to zero inches at the anterior end, the posterior end, and the lateral edge.

The at least one arch stability pad can comprise a crescent-shaped member having a generally wedge-shaped cross section corresponding in size and shape to the arch stability portion of the base insole, and having an anterior end, a posterior end, a medial edge, and a lateral edge, wherein the thickness of the at least one arch stability pad decreases from the center medial edge to the lateral edge, the anterior end and the posterior end. The at least one arch stability pad can range in thickness from a maximum of $3/16$ inch at the center medial edge to zero inch from the anterior end along the lateral edge to the posterior end.

The at least one arch stability pad can comprise a supplementary arch stability pad comprising a crescent-shaped member having a generally wedge-shaped cross-section for attachment to the at least one arch stability pad for increasing the maximum thickness of the at least one arch stability pad at the arch stability portion of the base insole, and having an anterior end, a posterior end, a medial edge, and a lateral edge, wherein the thickness of the supplementary arch stability pad decreases from the center medial edge to the lateral edge, the anterior end, and the posterior end. The supplementary arch stability pad can vary in thickness from a maximum of $3/16$ inch at the center medial edge to zero inch from the anterior end along the lateral edge to the posterior end.

The base insole can further comprise a resilient heel cushioning zone for cushioning impact to the heel. The resilient heel cushioning zone can comprise a pattern of cutout sections adapted to provide resilient cushioning immediately beneath the person's heel, or a low density gel pad adapted to provides resilient cushioning immediately beneath the person's heel. The low density gel pad can comprise a low density gel polymer.

In yet another embodiment, a subtalar joint inclinometer for measuring the lateral angular alignment of a person's foot when the person is in a standing position comprises, a base having a first portion adapted to be positioned beneath the heel of a person in a standing position and a second portion orthogonal with respect to the first portion and adapted to be placed adjacent to the Achilles tendon of the person whose heel is positioned on the base first portion; a heel alignment member adapted to be positioned on the heel of the person whose heel is positioned on the base first portion; and a protractor scale indicia on one of the base second portion and the heel alignment member and a reference line indicia on the other of the base second portion and the heel alignment member, wherein the reference line indicia is aligned with a zero position on the protractor scale indicia when the person's heel has a zero angular alignment and is adapted to indicate on the protractor scale indicia the degree of angular deviation of the person's foot from zero angular alignment. In one illustrative embodiment, the heel alignment member is pivotally mounted to the base. In another illustrative embodiment, the heel alignment member has wings which are adapted to cradle the heel of the person whose heel is positioned on the base first portion. In a preferred embodiment, the protractor scale indicia is disposed on the heel alignment member and the reference line indicia is disposed on the base second portion.

In a further embodiment of the invention, the subtalar joint inclinometer can also comprise a calcaneal bisection gauge for inscribing a reference line on the heel of the person aligned with the person's Achilles tendon and a protractor for determining the inclination of the reference line when the person is standing.

In yet another embodiment of the invention, a database for selecting at least one corrective alignment insole component for making a shoe correction for a misalignment of a person's foot based upon a measurement of a lateral angular alignment of the person's foot comprises a plurality of preselected lateral angular alignment values, and at least one corrective alignment insole component, wherein the preselected lateral angular alignment values are correlated to the at least one corrective alignment insole component so that the at least one corrective alignment insole component can be selected from the database based upon the lateral angular alignment measurement. The database can further include a correlation between the plurality of lateral angular alignment values with a variety of shoe types and wherein the appropriate corrective shoe can be selected for use with the selected at least one corrective alignment insole component. The at least one corrective alignment insole component can include at least one of a base insole, a supination control pad, a supplementary supination control pad, a motion control pad, and a supplementary motion control pad. A lateral angular alignment value of −5° to 3° can correlate to an assembly of corrective alignment insole components comprising a base insole, a supination control pad, and a supplementary supination control pad.

A lateral angular alignment value of 3° to 6° can correlate to an assembly of corrective alignment insole components comprising a base insole, and a supination control pad. A lateral angular alignment value of 6° to 9° can correlate to an assembly of corrective alignment insole components comprising a base insole. A lateral angular alignment value of 9° to 12° can correlate to an assembly of corrective alignment insole components comprising a base insole, and a supplementary motion control pad.

A lateral angular alignment value of 12° to 15° can correlate to an assembly of corrective alignment insole components comprising a base insole, and a motion control pad. A lateral angular alignment value of greater than 15° can correlate to an assembly of corrective alignment insole components comprising a base insole, a motion control pad, and a supplementary motion control pad.

BRIEF DESCRIPTION OF DRAWINGS

In the drawings:

FIG. 21 is a database chart according to the invention for selecting one or more pads for assembly into a corrective alignment insole to correct a misalignment of a foot.

FIG. 22 is a foot/leg symptomatic chart for correlating a corrective alignment insole with reported foot, leg, and hip symptoms according to the invention.

DETAILED DESCRIPTION

The foot has three main parts: the forefoot, the midfoot, and the hindfoot. The forefoot comprises the five toes, or phalanges, and their connecting long bones, i.e. the metatarsals. The midfoot comprises five irregularly-shaped tarsal bones, forms the foot's arch, and serves as a "shock absorber" during walking, running, or jumping. The bones of the midfoot are connected to the forefoot and the hindfoot by muscles and the plantar fascia, or the arch ligament. The hindfoot is composed of three joints and links the midfoot to the ankle, called the talus. The top of the talus is connected to the two long bones comprising the lower leg, i.e. the tibia and the fibula, forming a hinge that allows the foot to move up and down. The heel bone, or calcaneus is the largest bone in the foot. It joins the talus to form the subtalar joint, which enables the foot to rotate at the ankle.

Figure 1:
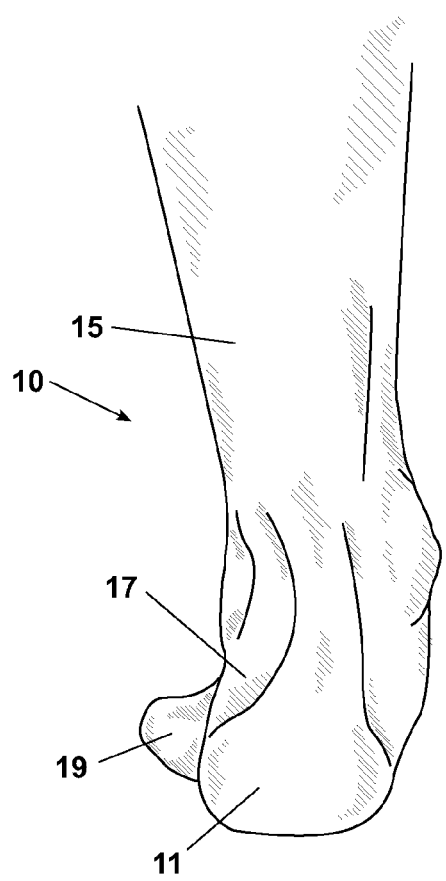
FIG. 1 is a rear elevational view of a human foot showing misalignment of the leg, ankle, and foot due to a fallen arch.

FIG. 1 shows a portion of a lower extremity 10 of a human illustrating misalignment of a heel 11, a leg 15, and ankle 17, and a foot 19 due to a structural anomaly. For exemplary purposes, the anomaly is shown as a condition commonly referred to as "fallen arches" or "flat feet." As a consequence of this condition, the ankle 17 is tilted inwardly, known as "pronation," and the lower leg 15 is inclined so that the foot 19, lower leg 15, knee, upper leg, and hip are vertically misaligned. This can result in an improper walking and running motion, placing the leg joints under stress, and increasing the potential for injury and pain.

Figure 2:
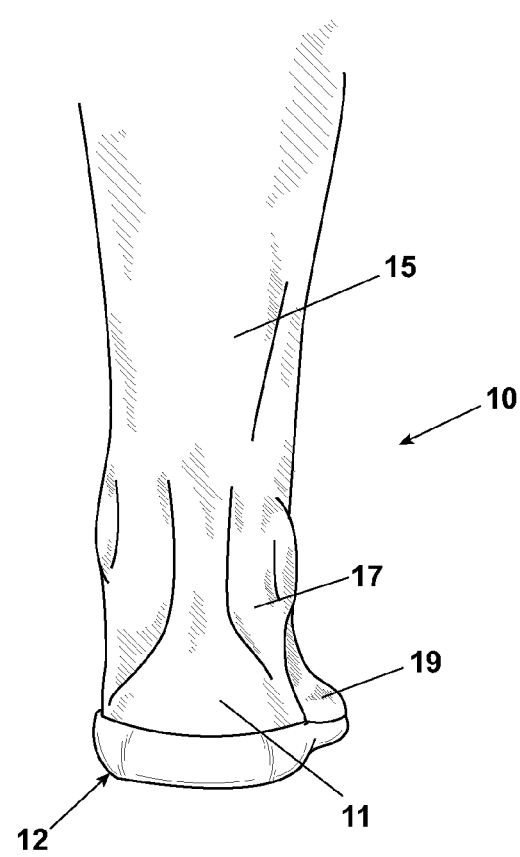
FIG. 2 is a rear elevational view of a human foot showing correction of the misalignment of FIG. 1 from the utilization of a corrective alignment insole according to the invention.

FIG. 2 shows a foot 19 supported on a corrective alignment insole 12 which corrects the misalignment of the foot due to, for example, "fallen arches" by raising the inner or medial portion of the foot 19 according to the invention. The corrective alignment insole 12 can also raise the outer or lateral portion of the foot 19 as necessary to correct other misalignments of the foot 19 and leg 15, as hereinafter described. The corrective alignment insole 12 also controls the motion of the foot 19 and the leg 15, restoring the proper alignment of the foot 19 and leg 15 during walking and running.

The corrective alignment insole 12 is a component system comprising a base insole and wedge-shaped pads of progressively increasing thickness for raising and tilting selected portions of the foot 19. The corrective alignment insole 12 can be readily customized to a precise foot structure and required alignment correction because of the adaptability of the component system. The combination of insole and pads required to correct the misalignment is determined by the use of two instruments comprising the invention and a systematic evaluation of the structure of the foot 19, the ankle, and the leg 15.

Figure 3:
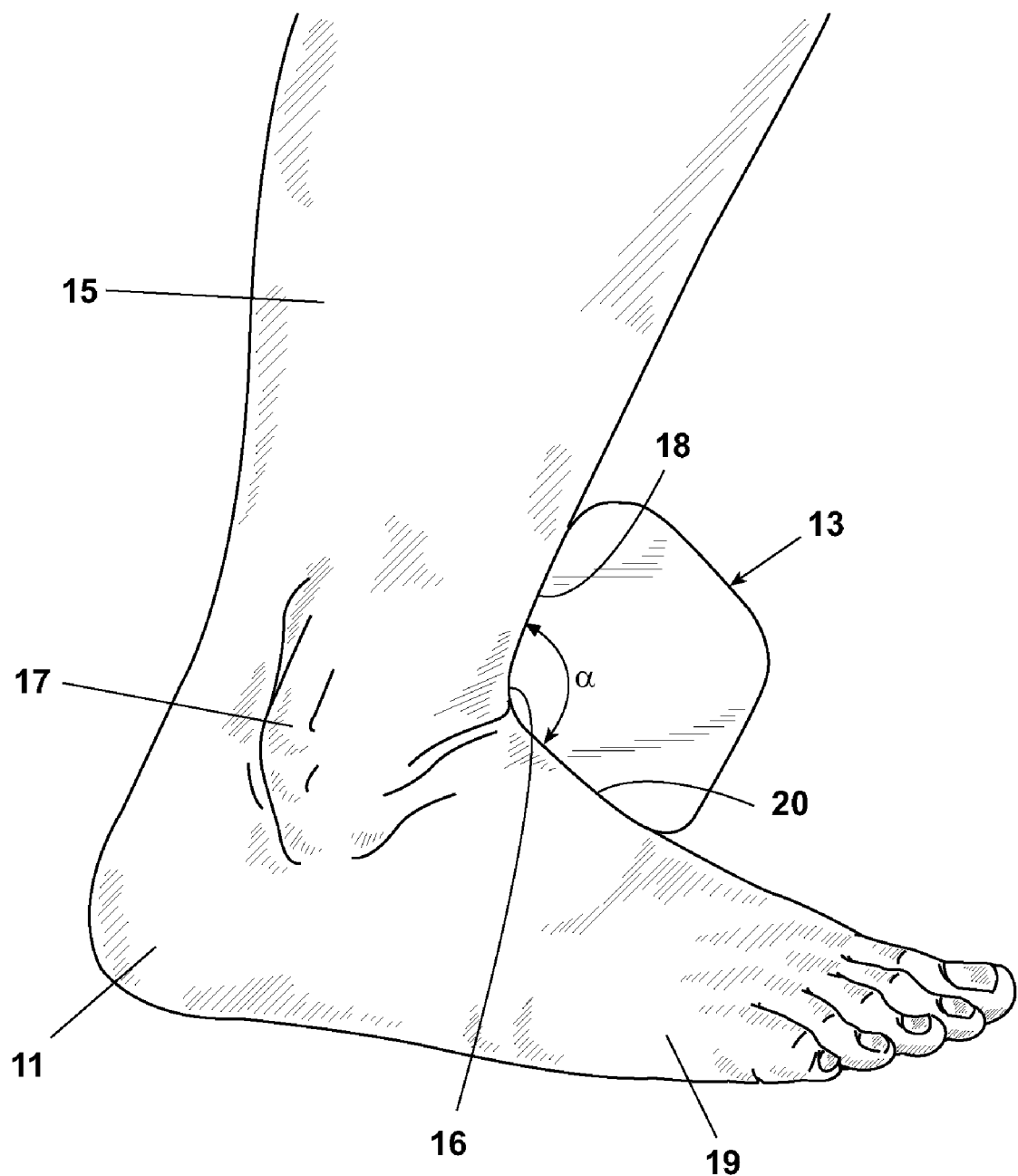
FIG. 3 is a side elevational view of a human foot showing the proper positioning of the leg, ankle, and foot utilizing a dorsiflexion template according to the invention.
Figure 4:
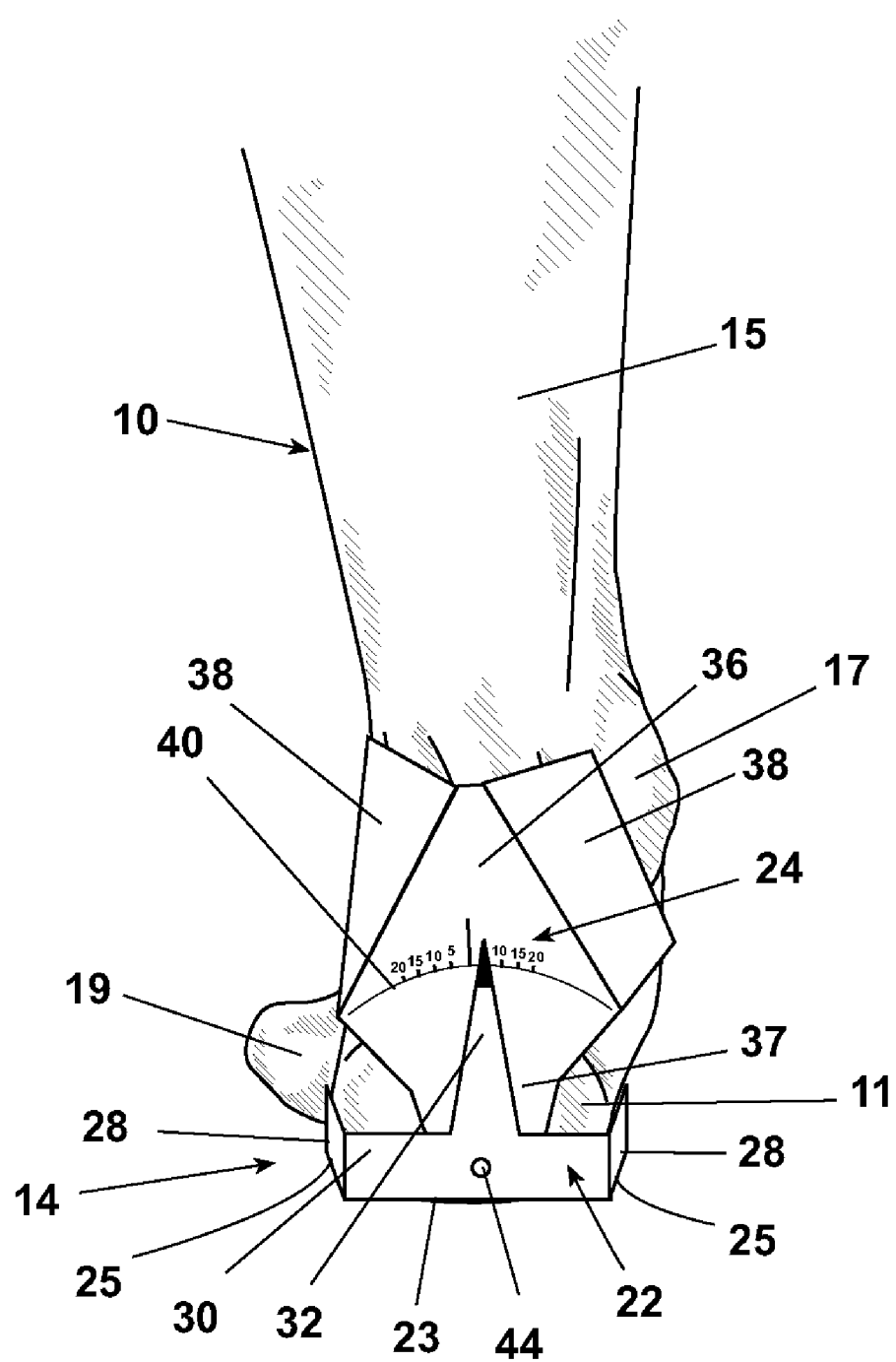
FIG. 4 is a rear elevational view of the foot of FIG. 3 showing the angular alignment of the leg, ankle, and foot utilizing a subtalar joint goniometer instrument according to the invention.
Figure 5:
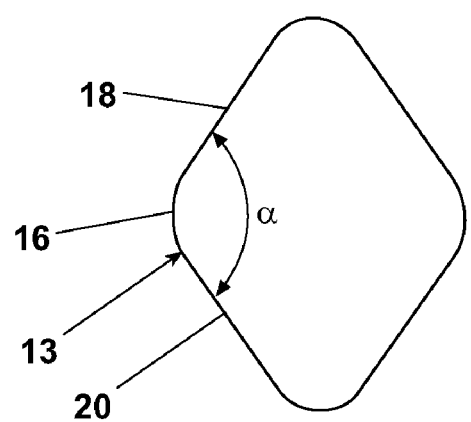
FIG. 5 is a plan view of the dorsiflexion template of FIG. 3.

FIGS. 3–7 show measuring instrumentation according to the invention. FIGS. 3–4 show the instrumentation in use. FIG. 3 shows the first instrument, referred to herein as a "dorsiflexion template" 13, positioned against the foot 19 at the ankle 17. Referring to FIG. 5, the dorsiflexion template 13 is a generally diamond-shaped, plate-like member having an ankle vertex 16, a upper edge 18, and a lower edge 20. The vertex 16, upper edge 18, and lower edge 20 define an obtuse angle α, preferably about 105°. The angle α represents the angle between the leg 15 and the foot 19 at which the heel 11 just begins to lift from a supporting surface as the leg 15 is inclined forward, typically at an angle of about 25° from the vertical.

Figure 6:
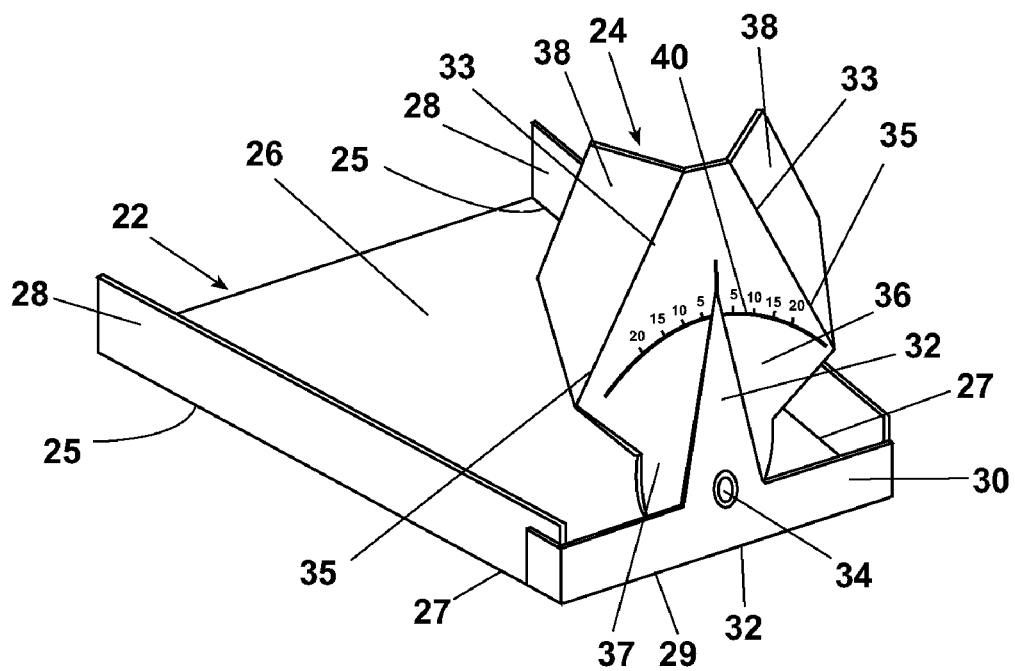
FIG. 6 is a perspective view of the subtalar joint goniometer instrument of FIG. 4.
Figure 7:
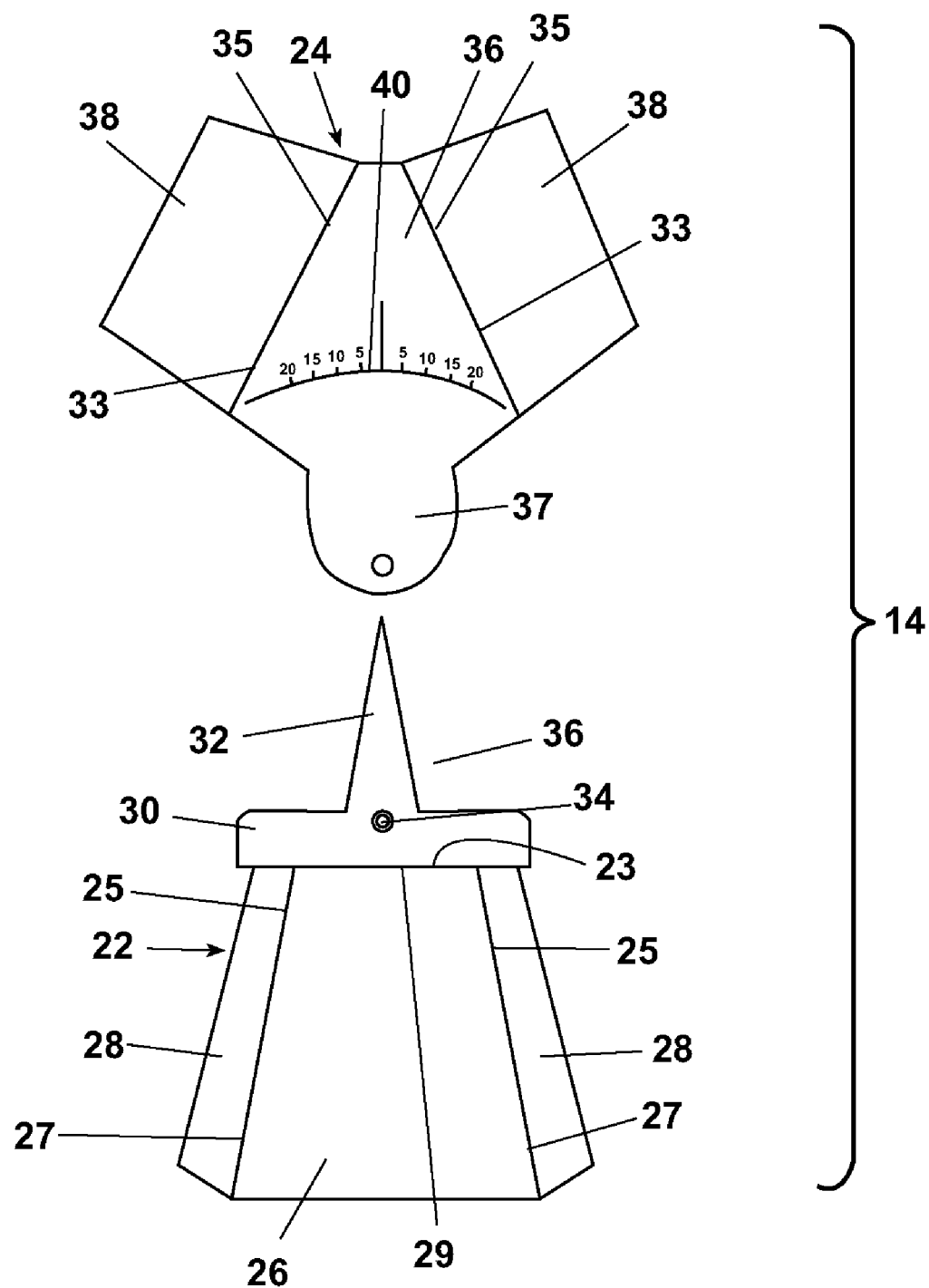
FIG. 7 is an exploded plan view of the subtalar joint goniometer instrument of FIG. 4.

Referring now to FIG. 4, a first embodiment of a subtalar joint inclinometer, referred to herein as a "subtalar joint goniometer" 14, is shown in position relative to the heel 11 for determining the lateral angular alignment of the foot 19. Referring also to FIGS. 6 and 7, the subtalar joint goniometer 14 is a two-piece, pivotably-interconnected angle measuring device comprising a base portion 22 and an alignment protractor 24. The base portion 22 is a generally trapezoidal-shaped, plate-like member comprising a heel plate 26, a pair of spaced apart upwardly-extending side walls 28 hingedly attached thereto, and an upwardly-extending rear wall 30 hingedly attached to the heel plate 26. The heel plate 26 is a generally trapezoidal-shaped member having a pair of spaced-apart edges 25 inclined toward the rear wall 30, and a rear edge 23. Each side wall 28 is attached to the heel plate 26 along the inclined edge 25 through a living hinge 27. The rear wall 30 is attached to the heel plate 26 along the rear edge 23 through a living hinge 29. As shown in FIG. 4, the heel plate 26, the side walls 28, and the rear wall 30 form a cradle-like structure into which the heel 11 is placed for measurement of the foot and leg alignment, as hereinafter described.

Extending upwardly from the rear wall 30, perpendicular to the heel plate 26, is a triangularly-shaped pointer 32. Extending through the back wall 30, in axial alignment with the pointer 32, is an aperture 34 for pivotably mounting the alignment protractor 24 to the base portion 22. In the preferred embodiment, the base portion 22 is formed from a sheet of material, such as a rigid plastic, or cardboard, and folded along the living hinges 27, 29 to form the cradle-like base portion 22.

The alignment protractor 24 is a generally irregularly-shaped member comprising an Achilles plate 36, a pair of spaced-apart wings 38 hingedly attached thereto, and an alignment scale 40 affixed to the Achilles plate 36, such as by printing or embossing. The Achilles plate 36 is an irregularly shaped member comprising a pair of spaced-apart inclined edges 33. Each wing 38 is a generally trapezoidal-shaped member extending laterally from the Achilles plate 36. Each wing 38 is attached to the Achilles plate 36 along the edge 33 through a living hinge 35. The lower portion of the Achilles plate 36 terminates in a downwardly-depending, arcuately-shaped pivot flange 37. The pivot flange 37 is provided with a generally centrally-positioned pivot aperture 42 adapted to be aligned with the aperture 34. A pin 44 is received through the pivot aperture 42 and the aperture 34 for pivotable movement of the alignment protractor 24 relative to the base portion 22. Preferably, the alignment protractor 24 is fabricated of the same material as the base portion 22.

The dorsiflexion template 13 and the subtalar joint goniometer 14 can be made available to the public through an Internet website for downloading to a printer. Printing or transferring the dorsiflexion template 13 and the subtalar joint goniometer 14 onto a stiff material, such as cardboard, will enable a consumer to fabricate the instruments for personal or family use.

Figure 18:
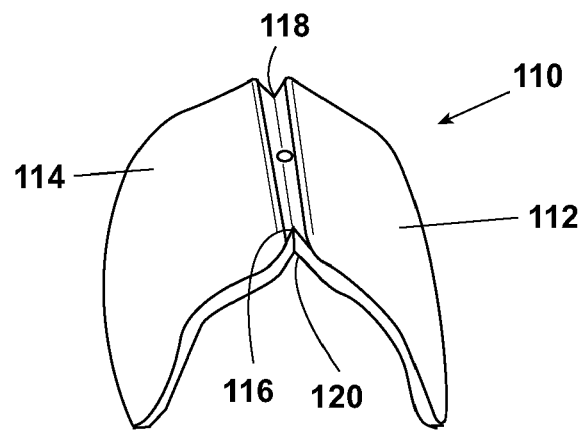
FIG. 18 a perspective view of a calcaneal bisection gauge according to the invention.
Figure 19:
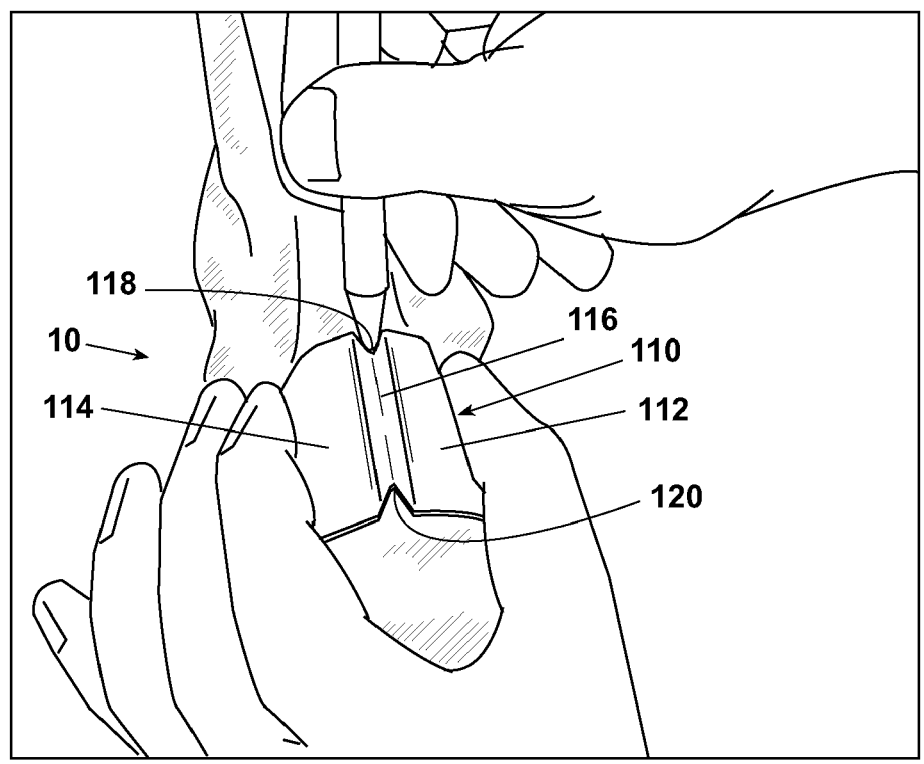
FIG. 19 is a perspective view of the use of the calcaneal bisection gauge of FIG. 18 to draw a calcaneal bisection line on a heel.
Figure 20:
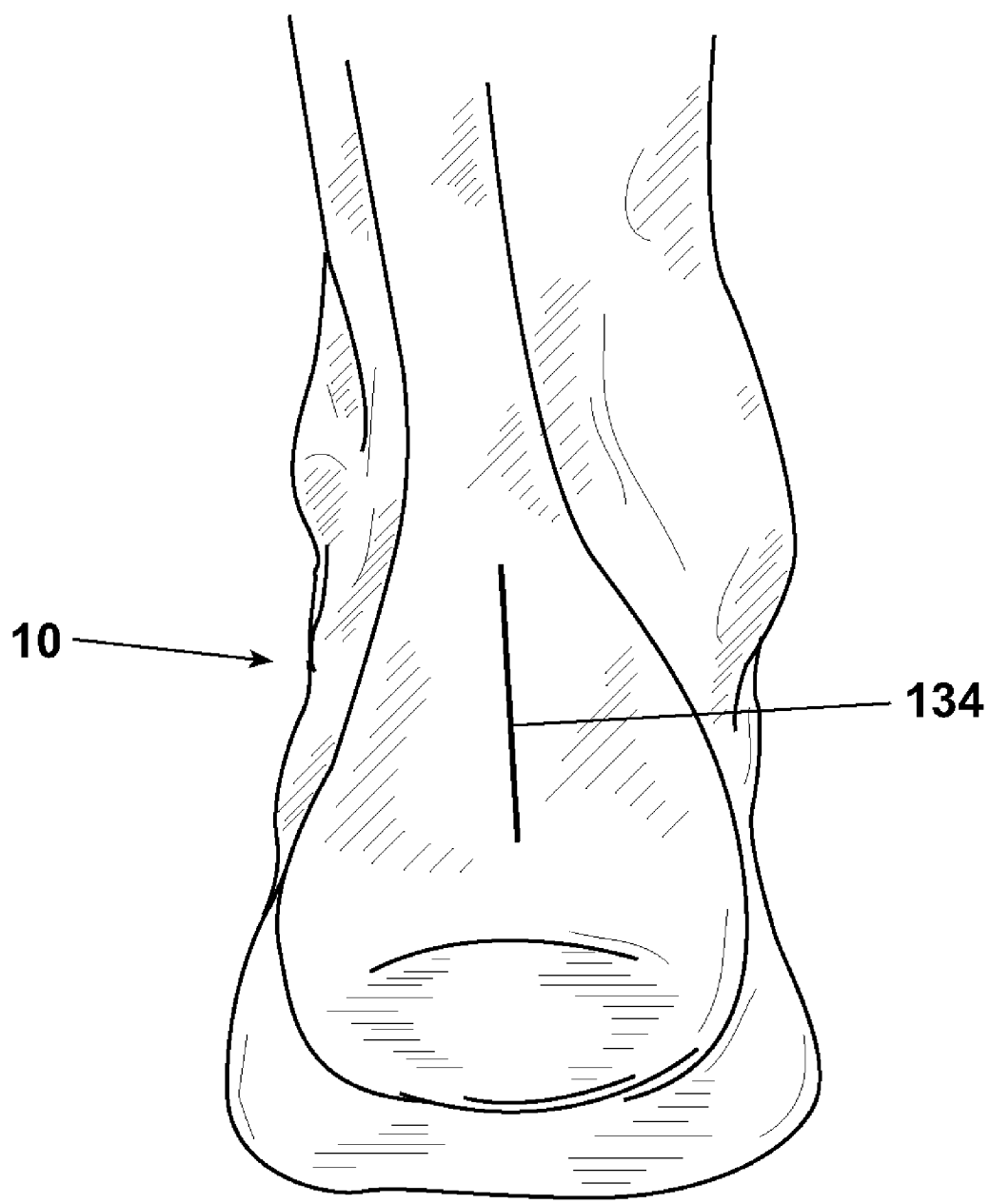
FIG. 20 is a rear elevational view of a foot showing the calcaneal bisection line drawn on the heel.
Figure 24:
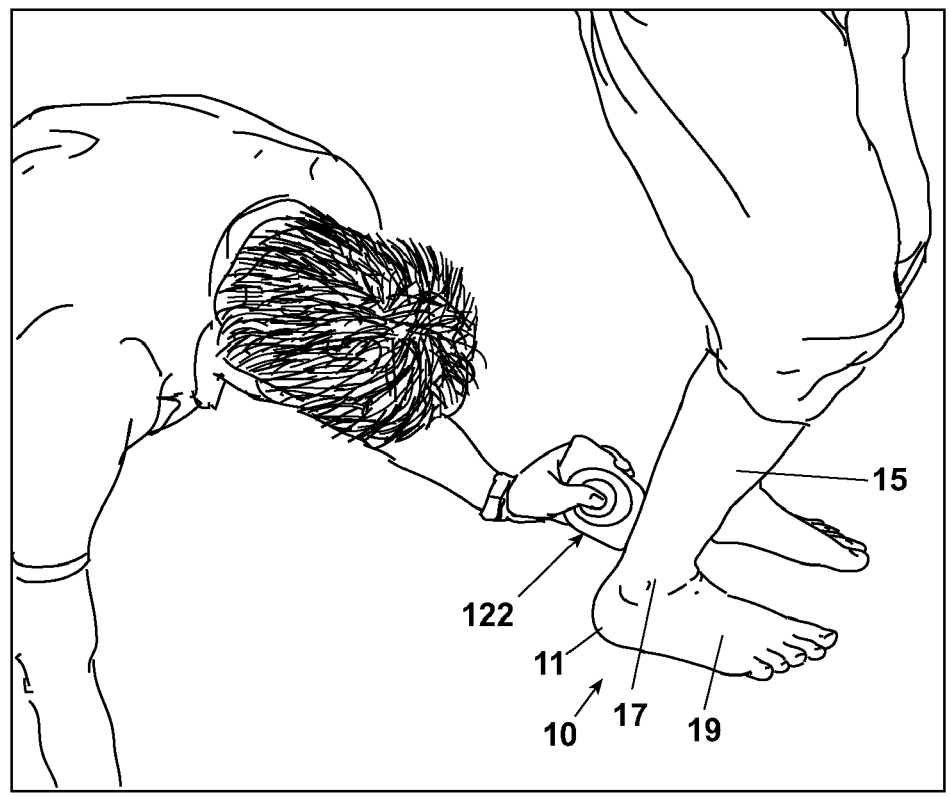
FIG. 24 is a perspective view of an evaluation of the angular misalignment of the foot width of the lower leg inclined 25°.

Referring to FIGS. 18, 19 and 24, an alternate subtalar joint inclinometer, comprising a calcaneal bisection gauge 110 and an angle finder 122, is shown. It is anticipated that the calcaneal bisection gauge 110 and the angle finder 122 will be used primarily by foot care professionals such as podiatrists and physicians. The calcaneal bisection gauge 110 is used to locate the mid-line of the heel 11, and comprises a pair of arcuate wings 112, 114 pivotably connected by a hinge 116. The calcaneal bisection gauge 110 can be fabricated of any suitable material, such as a rigid or semi-rigid plastic, aluminum, or stainless steel. The preferred embodiment comprises a thermoplastic with the hinge 116 integrally formed as a living hinge. The hinge 116 terminates at each end in a pair of generally V-shaped spaced-apart notches 118, 120 longitudinally aligned with the hinge 116. The curvature of the wings 112, 114 and the action of the hinge 116 enable the calcaneal bisection gauge 110 to "grip" the heel 11. As shown in FIG. 19, with the calcaneal bisection gauge 110 in position against the heel 11, a pair of angular marks are made on the heel 11 with a suitable marking instrument, such as a ball-point pen, and with the gauge 110 removed the apexes of the marks are connected to form a calcaneal bisection line 130 corresponding to the mid-line of the heel 11 (FIG. 20).

The angle finder 122 comprises a suitable conventional protractor, such as a conventional carpenter's protractor, as shown in FIG. 24, for determining the angle between the calcaneal bisection line 130 made using the calcaneal bisection gauge 110 and the vertical. The angle determined from the angle finder 122 is used to select the appropriate footwear corrective alignment insole pads, as hereinafter described.

FIGS. 8–17 show the various components of the corrective alignment insole pads according to the invention. The description which follows relates to corrective alignment insole pads that can be assembled and inserted into a shoe, preferably in place of the insole that is initially supplied with the shoe. However, the corrective alignment insole pads can also be initially incorporated into a shoe during manufacture so that the shoe is supplied to a purchaser with the corrective alignment insole pads already in place.

Referring to FIGS. 8–11, a base insole 50 comprises a generally plate-like foot-shaped member having a toe end 52 and a heel end 54. The base insole 50 may be flat, or somewhat curved to correspond to the general profile of the sole of a foot, particularly with a raised arch portion. The base insole 50 has an upper side 51 for contacting the foot 19, and an underside 53 for contacting the mid-sole of the footwear. In the preferred embodiment, the base insole 50 and hereinafter described pads are provided in a variety of lengths and widths to accommodate a suitable range of foot sizes.

Figure 8:
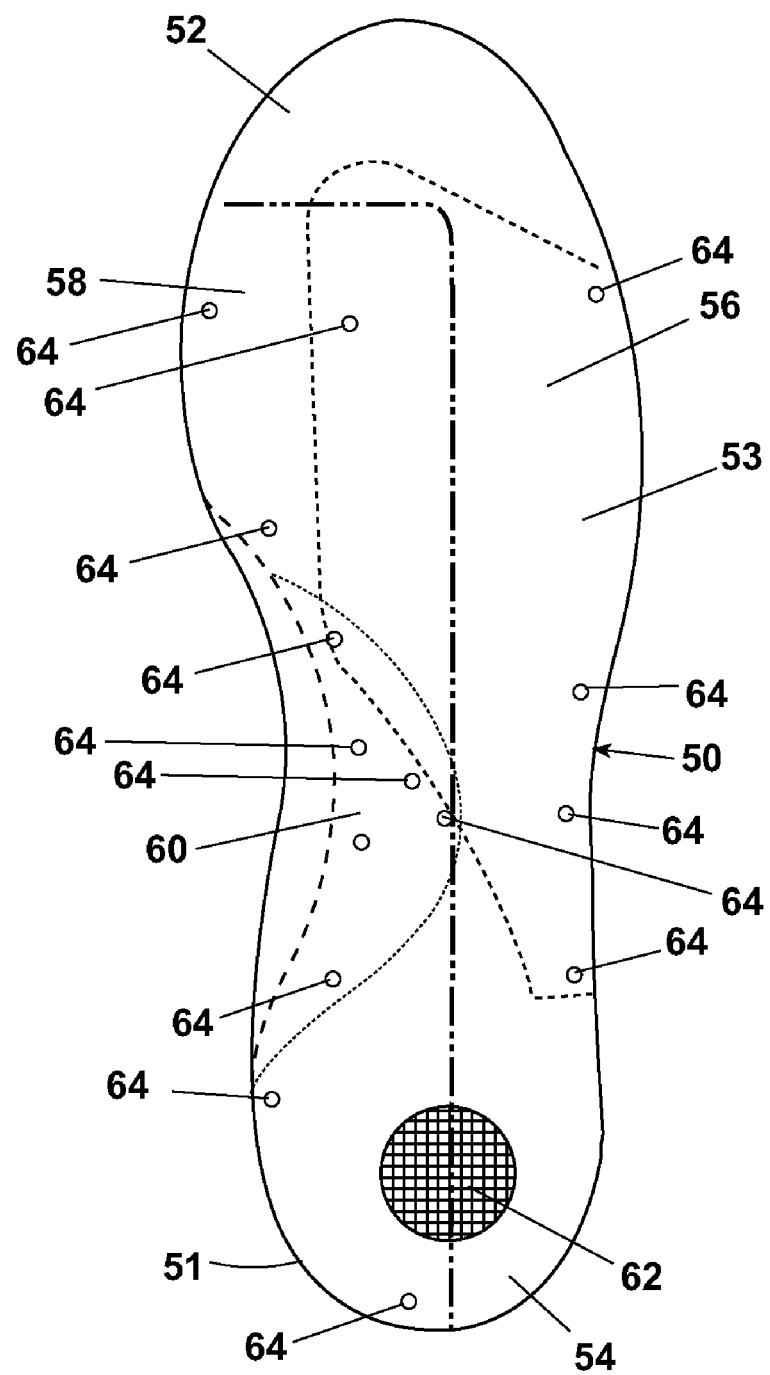
FIG. 8 is a bottom plan view of a base insole comprising a first component of a footwear corrective alignment insole according to the invention and an embodiment of a resilient heel cushioning zone.

The base insole 50 comprises a layered structure comprising a supporting shell, an overlying cellular foam layer, and a breathable polyester fabric cover. The shell is preferably fabricated of a semi-rigid plastic, such as polyurethane. The foam layer can be a closed-cell foam or an open-cell foam depending on the degree of cushioning and support desired. As shown in FIG. 8, the heel end 54 is provided with a heel shock absorption grid 62 generally at the center thereof, and comprising a pattern of cutout sections in the cellular foam layer which provides a resilient cushioning zone immediately beneath the heel 11. The underside 53 of the base insole 50 is provided with a plurality of selectively positioned alignment apertures 64 extending into the base insole 50.

Figure 28:
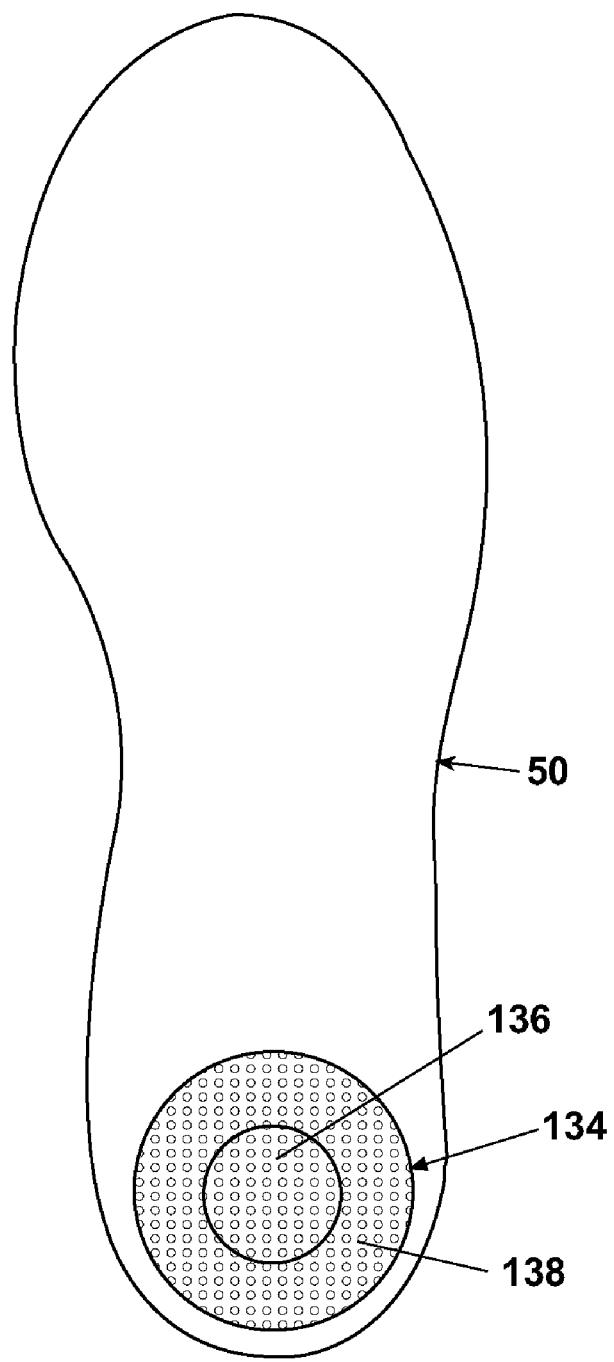
FIG. 28 is a plan view of the base insole shown in FIG. 8 comprising an alternate embodiment of a resilient heel cushioning zone comprising a low density gel pad.
Figure 29:
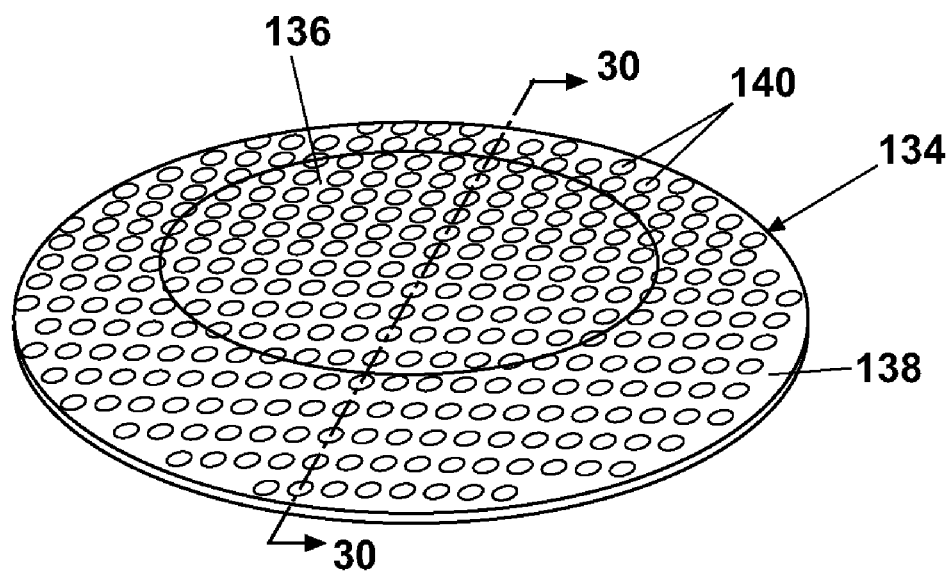
FIG. 29 is a perspective view of the low density gel pad shown in FIG. 28.
Figure 30:
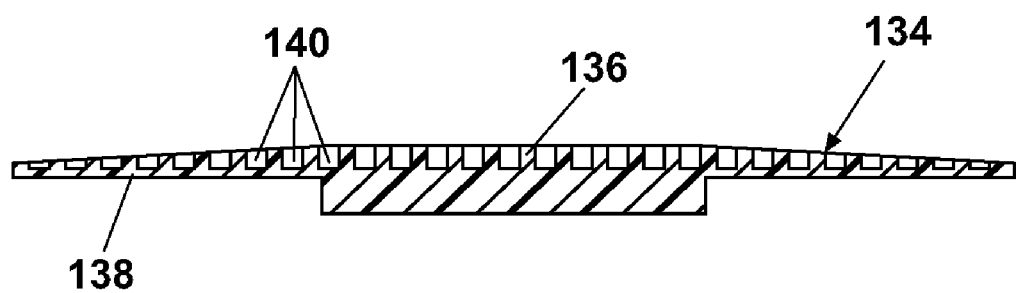
FIG. 30 is a sectional view of the low density gel pad shown in FIG. 29 taken along line 30—30 of FIG. 29.

An alternative resilient heel cushioning zone is shown in FIGS. 28–30. Instead of the heel shock absorption grid 62, a low density gel pad 134 is added to the heel end 54. The low density gel pad 134 is shown in FIGS. 28 and 29 as a circular-shaped pad comprising a circular center pedestal 136 with an annular perimeter flange 138 extending radially outwardly therefrom. Preferably, the perimeter flange 138 is tapered toward its perimeter. Alternatively, the gel pad 134 can be an oval or other shape suitable for incorporating into the heel end 54. As shown in FIGS. 29 and 30, the gel pad 134 is provided with a plurality of suitably-spaced circular recesses 140 adapted for controlling the cushioning properties of the pad 134. The size, number, and depth of the recesses 140 can be selected to provide a pre-selected degree of resilience and cushioning to the gel pad 134.

In the embodiment shown in FIGS. 28–30, the base insole 50 is provided with a circular recess or cutout adapted to receive the center pedestal 136 so that the perimeter flange 138 lays over the base insole 50. The insertion of the center pedestal 136 in the recess/cutout prevents the gel pad 134 from shifting during use. Preferably, the gel pad 134 comprises a low density gel polymer, although other materials can be employed based upon the degree of resilience and cushioning desired.

The base insole 50 is divided into a supination control portion 56 extending along the lateral portion of the base insole 50 (identified by the dotted line in FIG. 8), a motion control portion 58 extending along the medial portion of the base insole 50 (identified by the combined dashed and dotted line in FIG. 8), and an arch stability portion 60 extending along the arch portion of the base insole 50 (identified by the dotted line in FIG. 8).

Figure 9:
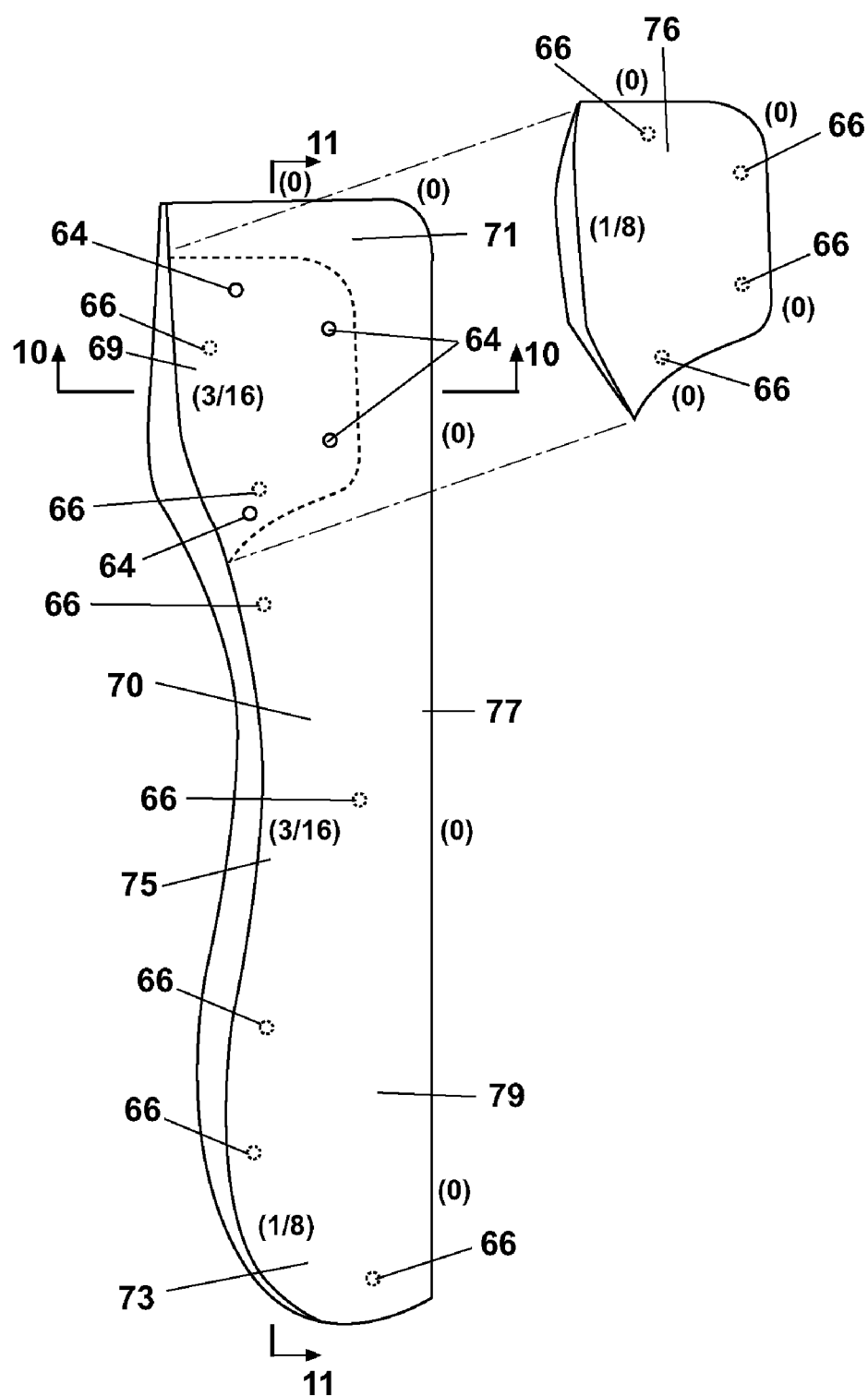
FIG. 9 is an exploded perspective view from underneath of a motion control pad and a supplementary motion control pad comprising a second component of a footwear corrective alignment insole according to the invention.
Figure 10:
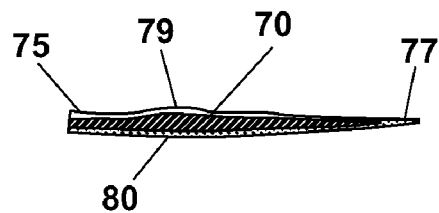
FIG. 10 is a sectional view of the motion control pad shown in FIG. 9 taken along line 10—10 of FIG. 9.
Figure 11:
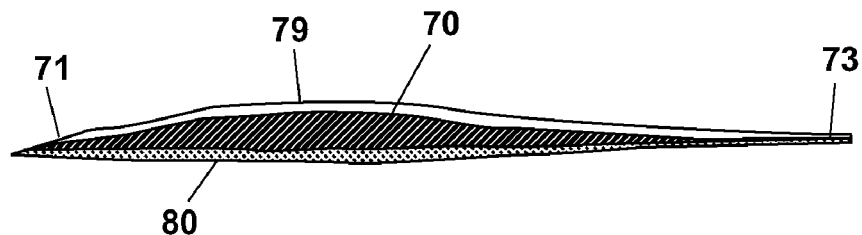
FIG. 11 is a sectional view of the motion control pad shown in FIG. 9 taken along line 11—11 of FIG. 9.

As shown in FIG. 9, a motion control pad 70 is an irregularly-shaped generally elongated member having a variable wedge-shaped cross section corresponding in size and shape to the motion control portion 58 of the base insole 50, and having an anterior end 71, a posterior end 73, a medial edge 75, a lateral edge 77, an obverse side 79, and a reverse side 80. The motion control pad 70 is preferably fabricated of EVA, with a cross-section as shown in FIGS. 10 and 11, and is attached to the underside 53 of the base insole 50 at the motion control portion 58. The thickness of the motion control pad 70 decreases from the medial edge 75 to the lateral edge 77, and from the portion along the medial edge 75 to the anterior end 71 and the posterior end 73. Preferably, the motion control pad 70 ranges in thickness from a maximum of 3/16-inch along the anterior portion of the medial edge 75, to 1/8-inch at the posterior end 73, to zero inches at the anterior end 71 and along the lateral edge 77. In FIG. 9, the thicknesses of the motion control pad 70 are indicated in parentheses.

The motion control pad 70 is provided with an irregularly-shaped supplementary motion control pad portion 69 located at the anterior medial portion of the motion control pad 70 (identified by the dotted outline in FIG. 9). The reverse side 80 of the motion control pad 70 is provided with a plurality of alignment posts 66 for insertion into the mating alignment apertures 64 of the motion control portion 58 of the base insole 50 for attaching the motion control pad 70 to the base insole 50. The obverse side 79 of the supplementary motion control pad portion 69 is provided with a plurality of selectively positioned alignment apertures 64 extending into the motion control pad 70.

As also shown in FIG. 9, a supplementary motion control pad 76 is an irregularly-shaped member, preferably fabricated of EVA, having a generally wedge-shaped cross-section corresponding in size and shape to the supplementary motion control pad portion 69, and is attached to the motion control pad 70 at the supplementary motion control pad portion 69 for increasing the maximum thickness of the motion control pad 70 at its anterior medial portion. The supplementary motion control pad 76 has an anterior end 100, a posterior end 102, a medial edge 104, a lateral edge 106, an obverse side 107, and a reverse side 108. Preferably, the supplementary motion control pad 76 varies in thickness from a maximum of 1/8 inch at the center medial edge 104 to zero inches at the anterior end 100, the posterior end 102, and the lateral edge 106.

The reverse side 108 of the supplementary motion control pad 76 is provided with a plurality of alignment posts 66 for insertion into the mating alignment apertures 64 of the supplementary motion control pad portion 69 for attaching the supplementary motion control pad 76 to the motion control pad 70. Alternatively, the supplementary motion control pad 76 can be attached directly to the base insole 50.

Figure 13:
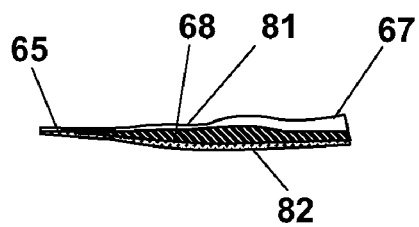
FIG. 13 is a sectional view of the supination control pad shown in FIG. 12 taken along line 13—13 of FIG. 12.
Figure 14:
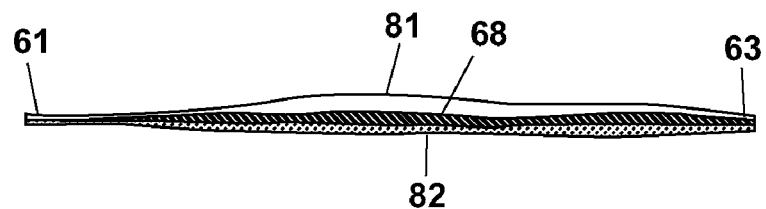
FIG. 14 is a sectional view of the supination control pad shown in FIG. 12 taken along line 14—14 of FIG. 12.
Figure 12:
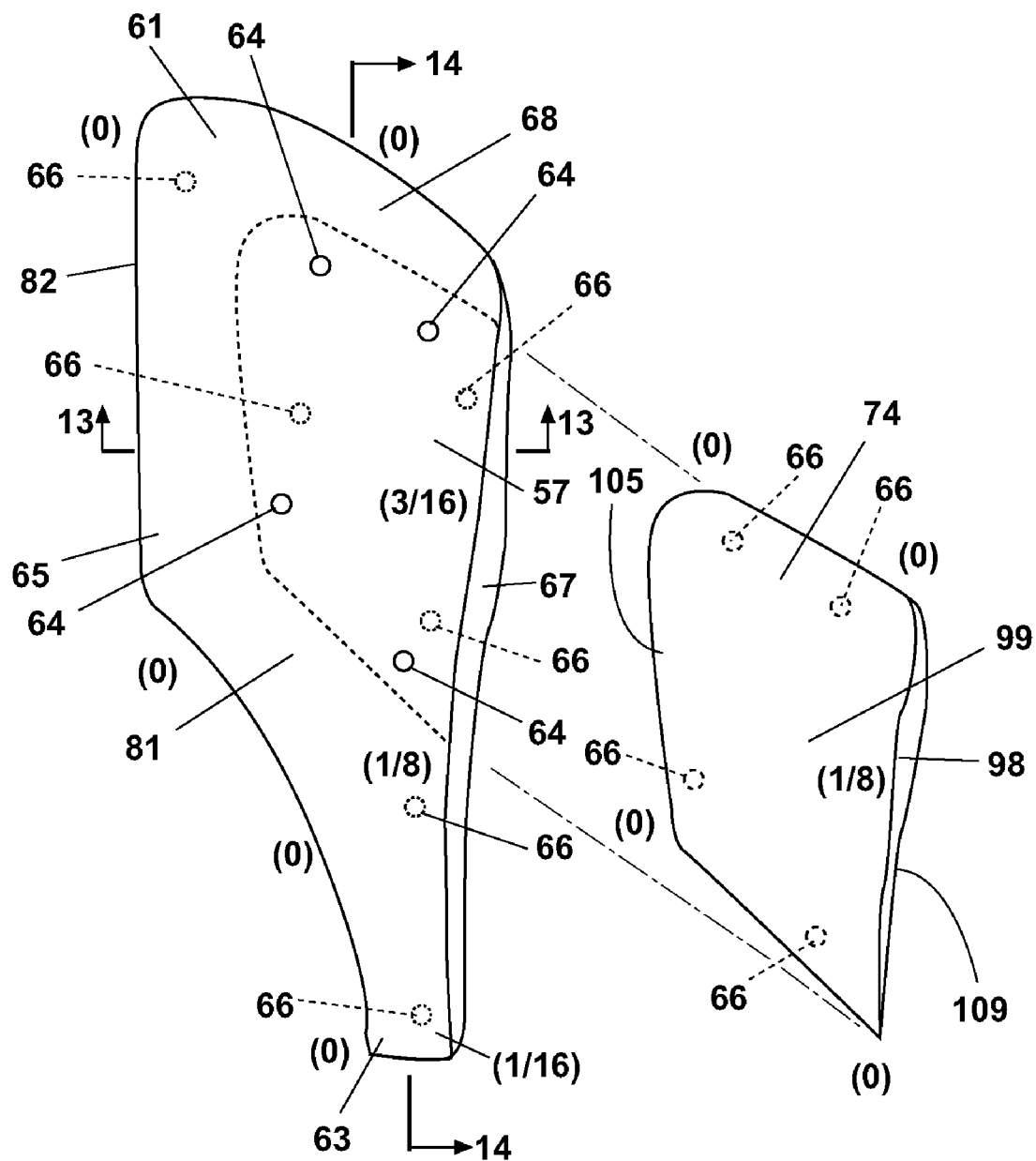
FIG. 12 is an exploded perspective view from underneath of a supination control pad and a supplementary supination control pad comprising a third component of a footwear corrective alignment insole according to the invention.

Referring now to FIG. 12, a supination control pad 68 is an irregularly-shaped member having a variable wedge-shaped cross section corresponding in size and shape to the supination control portion 56 of the base insole 50, and having an anterior end 61, a posterior end 63, a medial edge 65, a lateral edge 67, an obverse side 81, and a reverse side 82. The supination control pad 68 is preferably fabricated of EVA, with a cross section as shown in FIGS. 13 and 14, and is attached to the underside 53 of the base insole 50 at the supination control portion 56. The thickness of the supination control pad 68 decreases from the lateral edge 67 to the medial edge 65, and from the portion along the lateral edge 67 to the anterior end 61 and the posterior end 63. Preferably, the supination control pad 68 ranges in thickness from a maximum of 3/16 inch at the center lateral edge to 1/16 inch at the posterior end 63, to zero inches at the anterior end 61 and along the medial edge 65. In FIG. 12, the thicknesses of the supination control pad 68 are indicated in parentheses.

The supination control pad 68 is provided with an irregularly-shaped supplementary supination control pad portion 57 located at the center lateral portion of the supination control pad 68 (identified by the dotted outline in FIG. 12). The reverse side 82 of the supination control pad 68 is provided with a plurality of alignment posts 66 for mating communication with the alignment apertures 64 of the supination control portion 56 of the base insole 50 for attaching the supination control pad 68 to the base insole 50. The obverse side 81 of the supplementary supination control pad portion 57 is provided with a plurality of selectively positioned alignment apertures 64 extending into the supination control pad 68.

As also shown in FIG. 12, a supplementary supination control pad 74 is an irregularly-shaped member, preferably fabricated of EVA, having a generally wedge-shaped cross section corresponding in size and shape to the supplementary supination control pad portion 57, and is attached to the supination control pad 68 at the supplementary supination control pad portion 57 for increasing the maximum thickness of the supination control pad 68 at its center lateral portion. The supplementary supination control pad 74 has an anterior end 101, a posterior end 103, a medial edge 105, a lateral edge 98, an obverse side 99, and a reverse side 109. Preferably, the supplementary supination control pad 74 varies in thickness from a maximum of 1/8 inch at the center lateral edge 98 to zero inches at the anterior end 101, the posterior end 103, and the medial edge 105.

Figure 15:
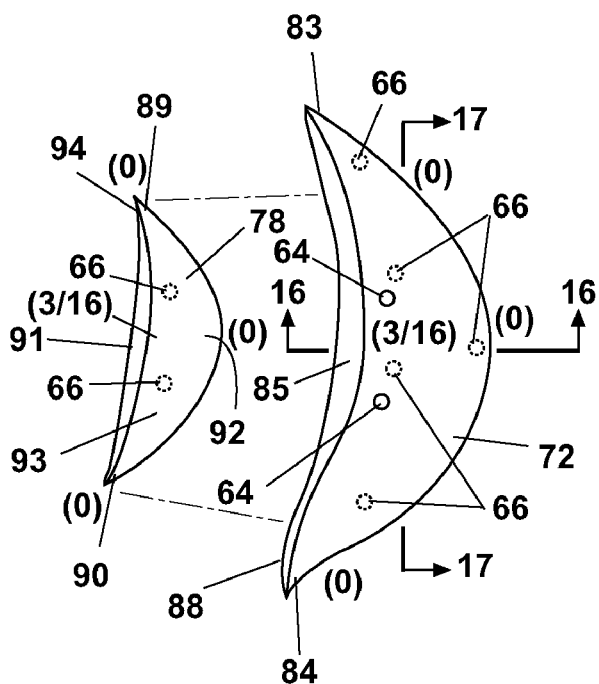
FIG. 15 is an exploded perspective view from underneath of an arch stability pad and a supplementary arch stability pad comprising a fourth component of a footwear corrective alignment insole according to the invention.
Figure 16:
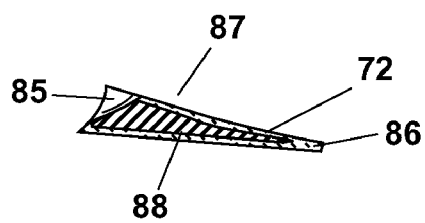
FIG. 16 is a sectional view of the arch stability pad shown in FIG. 15 taken along line 16—16 of FIG. 15.
Figure 17:
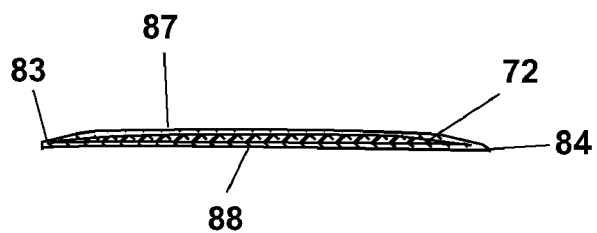
FIG. 17 is a sectional view of the arch stability pad shown in FIG. 15 taken along line 17—17 of FIG. 15.

As shown in FIG. 15, an arch stability pad 72 is a generally crescent-shaped member having a generally wedge-shaped cross section corresponding in size and shape to the arch stability portion 60 of the base insole 50, and having an anterior end 83, a posterior end 84, a medial edge 85, a lateral edge 86, an obverse side 87, and a reverse side 88. The arch stability pad 72 is preferably fabricated of EVA, with a cross-section as shown in FIGS. 16 and 17, and is attached to the underside 53 of the base insole 50 at the arch stability portion 60. The thickness of the arch stability pad 72 decreases from the center medial edge 85 to the lateral edge 86, the anterior end 83 and the posterior end 84. Preferably, the arch stability pad 72 ranges in thickness from a maximum of 3/16 inch at the center medial edge 85 to zero inch from the anterior end 83 along the lateral edge 86 to the posterior end 84. In FIG. 15, the thicknesses of the arch stability pad 70 are indicated in parentheses.

The reverse side 88 of the arch stability pad 72 is provided with a plurality of alignment posts 66 for mating communication with the alignment apertures 64 of the arch stability portion 60 of the base insole 50 for attaching the arch stability pad 72 to the base insole 50. The obverse side 87 of the arch stability pad 72 is provided with a plurality of selectively positioned alignment apertures 64 extending into the arch stability pad 72 for attachment of a supplemental arch stability pad 78.

As also shown in FIG. 15, a supplementary arch stability pad 78 is a generally crescent-shaped member, preferably fabricated of EVA, having a generally wedge-shaped thickness for attachment to the arch stability pad 72 for increasing the maximum thickness of the arch stability pad 72 at the arch stability portion 60 of the base insole 50. The supplementary arch stability pad 78 has an anterior end 89, a posterior end 90, a medial edge 91, a lateral edge 92, an obverse side 93, and a reverse side 94. Preferably, the supplementary arch stability pad 78 varies in thickness from a maximum of 3/16 inch at the center medial edge 91 to zero inch from the anterior end 89 along the lateral edge 92 to the posterior end 90. In FIG. 15, the thicknesses of the supplemental arch stability pad 78 are indicated in parentheses.

Figure 27:
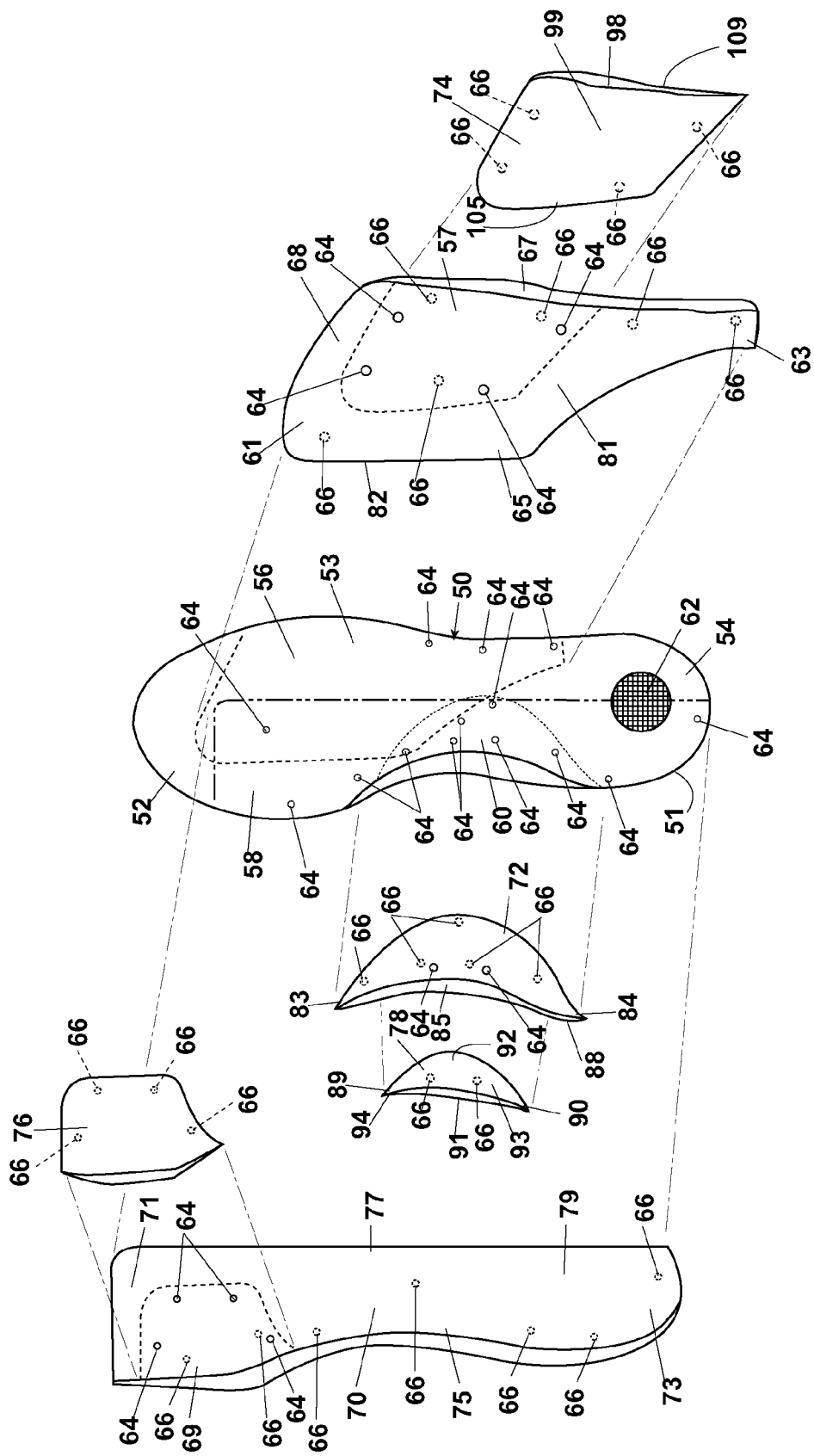
FIG. 27 is an exploded view showing the assembly of the pads of FIGS. 9, 12, and 15 onto the base insole of FIG. 8 to form a corrective alignment insole according to the invention.

FIG. 27 shows the base insole 50 with the proper positioning of the supination control pads 68, 74, the motion control pads 70, 76, and the arch stability pads 72, 78 on the underside 53 of the base insole 50 to form the corrective alignment insole 12 as herein described. The insole 50 can be utilized with or without pads as determined by the measurements described herein. The measurements are used to determine specific pads to be attached to the base insole 50 to form a corrective alignment insole 12, as hereinafter described. The corrective alignment insole 12, incorporating selected pads, can be utilized as an insole to be placed by the user in a selected shoe after removing the original insole. In such a case, only one pair of corrective alignment insoles 12 is needed. Alternatively, a corrective alignment insole as described herein can be incorporated into a shoe as the original insole, thereby rendering the shoe a complete corrective alignment shoe. A user would then select a style of shoe having the required corrective alignment insole already installed.

FIG. 21 shows a database embodied in a chart for determining the particular combination of corrective alignment insole components needed based upon the results from the measurements obtained with the dorsiflexion template 13 and the subtalar joint goniometer 14, or alternatively the calcaneal bisection gauge 110 and the angle finder 122. FIG. 22 shows a foot/leg symptomatic database embodied in a chart for use with the database chart of FIG. 21 for refining the selection of corrective alignment insole components based upon a patient's description of various foot and leg symptoms. Alternatively, the databases can be embodied in a suitable alternate form, such as a computer database in digital form, or the like. These databases are used as part of a diagnostic and therapeutic method for systematically evaluating the misalignment of the patient's foot and leg, and selecting the necessary corrective alignment insole pads to correct the misalignment and reducing the patient's symptoms. This diagnostic and therapeutic method will now be described.

It is anticipated that the dorsiflexion template 13 and the subtalar joint goniometer 14 will be utilized by footwear sales personnel and the consumer, whereas the calcaneal bisection gauge 110 and the angle finder 122 will be used by podiatrists, orthopedic surgeons, and other footcare specialists. However, it will be understood that the use of the instruments is not so limited and that any of the instruments can be successfully utilized by a person having an understanding of their proper use.

There are five generally-recognized foot types which are quantified through the use of the method and instruments described herein. These include over-supination, mild supination, neutral, mild pronation, and over-pronation. The unique method described herein further divides over-pronation into two subcategories based upon the degree of angular displacement of the foot. Supination refers to the tendency of the foot to roll outwardly or laterally during walking or running. Pronation refers to the tendency of the foot to roll inwardly or medially during walking or running. The patient's description of his or her foot and leg symptoms is used with the foot/leg symptomatic chart (FIG. 22) to identify likely corrective alignment insole pads and any medical conditions that may require additional diagnosis and treatment.

Shoes are frequently manufactured with selected structural qualities to accommodate the different foot types described herein. Thus, certain shoes will be preferred for a pronating foot, while other shoes will be preferred for a supinating foot. These shoe types and the associated foot types are set out in the foot/leg symptomatic chart of FIG. 22. The measurements obtained with the dorsiflexion template 13 and the subtalar joint goniometer 14, or the calcaneal bisection gauge 110 and the angle finder 122, are used to place the patient's foot into one of the above foot types using the measurement chart (FIG. 21), select a recommended shoe type, and select the corrective alignment insole components.

For example, having determined the angular alignment of the foot as herein described and obtained a measurement of 10 degrees, the database chart prescribes a shoe providing full stability having a corrective alignment insole to correct mild pronation comprising a neutral base insole 50 with a supplementary motion control pad 76, identified in the measurement chart 130 as a "D" corrective alignment insole.

The dorsiflexion template 13 and the subtalar joint goniometer 14 are utilized as shown in FIGS. 3 and 4. The dorsiflexion template 13 is placed at the front apex of the ankle 17 between the leg 15 and the foot 19, and the leg 15 is inclined forward so that the leg 15 contacts the upside per side 18 of the dorsiflexion template 13 and the foot 19 contacts the lower side 20 of the dorsiflexion template 13, thus orienting the leg 15 at the proper inclination for use of the subtalar joint goniometer 14. While the inclination of the leg 15, as determined with the dorsiflexion template 13, is maintained, the heel 11 is placed on the heel plate 26 in contact with the alignment protractor 24 so that the heel 11 can be "wrapped" with the wings 38, as shown in FIG. 4. The alignment protractor 24 will thus be placed in proper orientation relative to the heel 11 and the ankle 17. The angular alignment of the heel 11 and the ankle 17 can then be read from the alignment protractor 24. The angle thus determined is used with the database chart of FIG. 21 to select the proper corrective alignment insole 12 and footwear.

Alternatively, a footcare professional can use the dorsiflexion template 13 and the subtalar joint goniometer 14, or the calcaneal bisection gauge 110 and the angle finder 122, in combination with a medical evaluation, to determine the angle of alignment and the proper corrective alignment insole 12 and footwear from the database chart of FIG. 21. The following description assumes that the footcare professional will utilize the calcaneal bisection gauge 110 and the angle finder 122.

Preferably, a sequence of specific steps is taken in utilizing the invention. The method of utilizing the information to select a corrective alignment insole includes a sequence of evaluation steps comprising a standing visual assessment or "weight-bearing" assessment, a non-weight-bearing or prone measurement, and subtalar joint measurements using the subtalar joint goniometer 14. The standing visual assessment and prone measurement involve observational and diagnostic techniques familiar to a person of ordinary skill in orthopedics, podiatry, and other medical arts related to the feet, although these techniques are utilized in a novel way in conjunction with the unique subtalar joint measurements to identify the proper corrective alignment insole.

Figure 23:
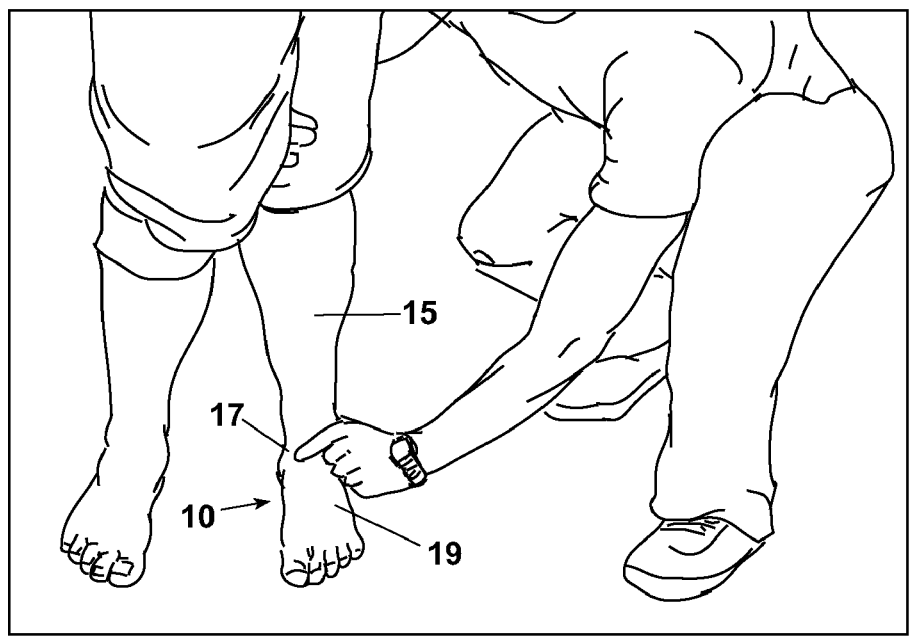
FIG. 23 is a perspective view of an evaluation of a subtalar neutral position.

During the "weight-bearing" assessment, three measurements are taken. The first is an evaluation of the subtalar neutral position. The evaluation is performed with a patient initially in a prone position. With the patient in the prone position, the calcaneal bisection gauge 110 is used to establish the calcaneal bisection line 130 as heretofore described. The patient then stands with his or her knees approximately four inches apart (i.e. a "fist width" apart). The medial and lateral heads of the talus bone are palpated while the patient rotates his or her hips from side to side until both heads of the talus bone can be palpated evenly on both sides (FIG. 23). While the patient holds that position, the subtalar joint goniometer 14 or angle finder 122 are used to determine the heel angle. This angle defines the subtalar neutral position, and is recorded.

The next measurement is an evaluation of the "relaxed" position. The patient stands in an upright, relaxed posture with the feet slightly apart in a natural position. A second measurement of the heel angle is taken and recorded.

The final measurement defines 25° of standing dorsiflexion. For this measurement, the patient stands with his or her feet spread slightly apart and squats until the Achilles area of the heel 11 is inclined 25° from the vertical. Twenty-five degrees is determined either by a direct angular measurement using the angle finder 122, as shown in FIG. 24, or by using the dorsiflexion template 13. While the patient holds this position, the heel angle, as defined by the calcaneal line, is determined and recorded.

Figure 25:
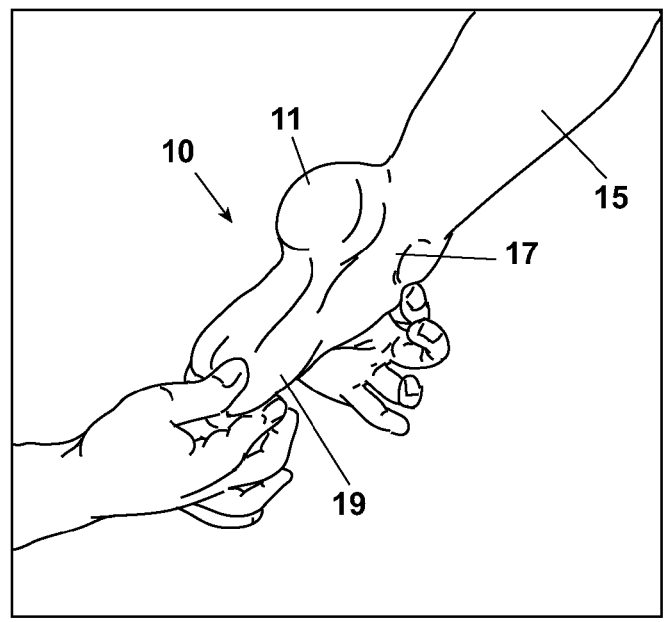
FIG. 25 is a perspective view of a non-weight bearing evaluation of the alignment of the foot.
Figure 26:
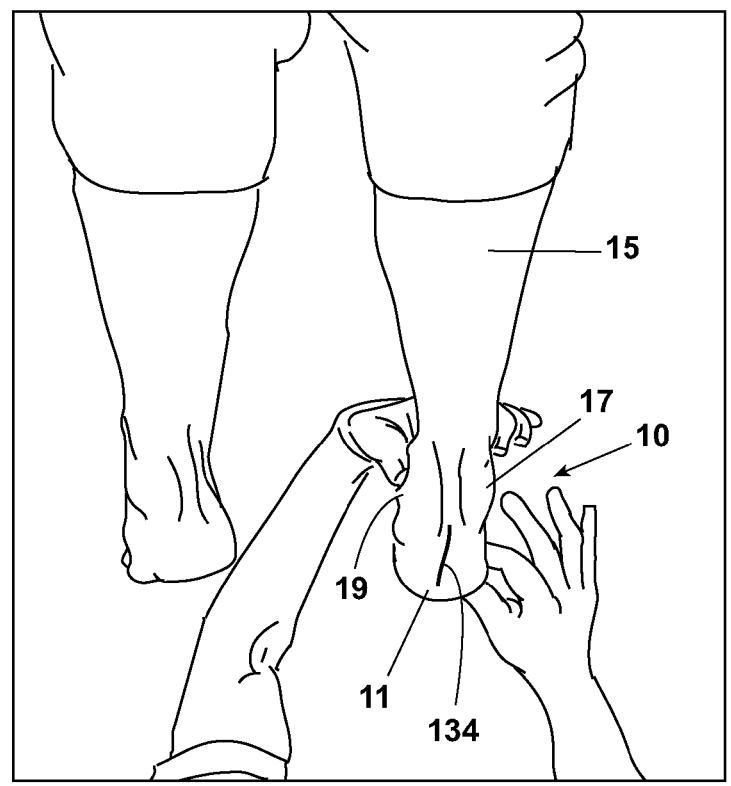
FIG. 26 is a view of a foot and a leg of a patient lying in a prone position showing a non-weight bearing evaluation of the alignment of the foot.

The non-weight-bearing assessment is performed with the patient lying face-down on an evaluation table with both feet extending off the edge of the table. Both heads of the talus bone are palpated while the fifth metatarsal head is grasped so that the ankle 17 can be rotated from side to side (FIG. 25). The ankle 17 is rotated until the talus heads are even on both sides. When the point is reached at which the talus heads are even, gentle pressure is placed on the bottom of the fifth metatarsal head to force the foot into dorsiflexion (FIG. 26). The foot will assume one of three orientations: neutral, i.e. effectively no misalignment, varus, i.e. a supinated alignment, or valgus, i.e. a pronated alignment. These findings are recorded for later reference.

The following represents expected normal ranges of measurement:
Weight-Bearing: 0°–3°
Non-Weight-Bearing: 4°–6°
Standing Dorsiflexion: 7°–9°

The difference between the weight-bearing measurement and the standing dorsiflexion measurement represents the total pronation. A value of 6° or less frequently indicates a tendency toward oversupination. A value of 10° or greater frequently indicates a tendency toward over-pronation. If the weight-bearing measurement is different than the non-weight-bearing measurement, the foot is referred to as a "compensated foot." Conversely, if the weight-bearing measurement is the same as the non-weight-bearing measurement, the foot is referred to as an "uncompensated foot."

The total pronation measurement, i.e. the difference between the weight-bearing measurement and the standing dorsiflexion measurement, is used to determine the correct corrective alignment insole from the database chart (FIG. 21). The database chart is also utilized to identify the shoe type with which the corrective alignment insole should be used. The foot/leg symptomatic chart (FIG. 22) can also be used as an initial diagnostic chart or to further confirm or refine the selection of the corrective alignment insole type from the database chart. The symptomatic chart identifies common symptoms which many patients describe and which can be alleviated by the proper corrective alignment insole. For example, the foot/leg symptomatic chart indicates that lateral shin pain may be alleviated through a type A or B corrective alignment insole. A total pronation measurement of 4°, indicating mild supination and the use of a type B corrective alignment insole, would confirm the selection of a type B corrective alignment insole as indicated by the patient's complaint of lateral shin pain.

As an alternative to the database chart shown in FIG. 21, the subtalar joint goniometer measurements can be incorporated into a computerized database and correlated with shoe type information and specific combinations of corrective alignment insole components in a computerized program for quickly selecting proper shoe types and corrective alignment insole components for a range of subtalar joint goniometer measurements.

The method of measuring the alignment of a foot and the selection of a shoe type and corrective alignment insole components can be formalized into a sequence of steps, which can be incorporated into a comprehensive computer program.

The method can include the following steps:
While standing, inclining the leg approximately 25° from the vertical utilizing a dorsiflexion template;
While maintaining the leg in the inclined position, taking a measurement of the lateral angular alignment of the foot utilizing a subtalar joint goniometer;
Reading the lateral angular alignment value from the subtalar joint goniometer;
Referring the lateral angular alignment value to a database chart which correlates a range of lateral angular alignment values from a subtalar joint goniometer with shoe types and combinations of corrective alignment insole components;
Selecting a shoe type and a combination of corrective alignment insole components from the database chart corresponding to the lateral angular alignment value obtained from the subtalar joint goniometer measurement;
Constructing a corrective alignment insole from a base insole and one or more supination or pronation control pads and arch control pads identified in the database chart corresponding to the lateral angular alignment value obtained from the subtalar joint goniometer measurement; and
Utilizing the corrective alignment insole to correct the alignment of the foot by incorporating the corrective alignment insole into the shoe type identified in the database chart corresponding to the lateral angular alignment value obtained from the subtalar joint goniometer measurement.

Prevention and correction of biomechanical injuries to the lower extremities is possible with the novel corrective system described herein. Utilizing the unique measuring tools as described herein, footcare specialists, shoe stores, and consumers can select appropriate footwear and a customized corrective alignment insole quickly and accurately, thereby enhancing the effectiveness of the foot alignment correction and decreasing costs. Unlike prior art corrective alignment insoles, the novel corrective system described herein focuses corrective action away from the arch alone and onto the entire foot and its biomechanical behavior during walking or running. The corrective alignment insole can be accurately customized by selecting a specific combination of the unique support pads for any of six different foot types and arch heights. Ankle mobility is controlled using support pads specifically configured and combined for motion control, stability, neutral conditions, or supination control.

While the invention has been specifically described in connection with certain specific embodiments thereof, it is to be understood that this is by way of illustration and not of limitation, and the scope of the appended claims should be construed as broadly as the prior art will permit.

What is claimed is:

1. A method of making a shoe correction for the alignment of a person's foot, comprising the steps of:
    while the person is standing on the foot, inclining the person's lower leg forwardly about the foot a preselected angle from the vertical; and
    while maintaining the person's lower leg in the forward inclined position at the preselected angle, measuring the lateral angular alignment of the foot.

2. A method of making a shoe correction for the alignment of a person's foot according to claim 1 and further comprising the step of selecting from a database appropriate corrective components for incorporation into a shoe to correct the alignment of the person's foot.

3. A method of making a shoe correction for the alignment of a person's foot according to claim 2 wherein the database has a correlation between a range of lateral angular alignment values and appropriate corrective components.

4. A method of making a shoe correction for the alignment of a person's foot according to claim 3 wherein the corrective components include combinations of corrective alignment insole components.

5. A method of making a shoe correction for the alignment of a person's foot according to claim 4 wherein the corrective alignment insole components include supination, pronation, and arch control pads.

6. A method of making a shoe correction for the alignment of a person's foot according to claim 5 and further comprising the step of constructing a corrective alignment insole from a base insole and the selected supination, pronation, and arch control pads.

7. A method of making a shoe correction for the alignment of a person's foot according to claim 6 wherein the database further includes a correlation between lateral angular alignment values and an appropriate shoe type.

8. A method of making a shoe correction for the alignment of a person's foot according claim 7 and further comprising the step of incorporating the corrective alignment insole into the selected shoe type.

9. A method of making a shoe correction for the alignment of a person's foot according to claim 8 wherein the measuring step is carried out with the aid of a subtalar joint goniometer.

10. A method of making a shoe correction for the alignment of a person's foot according to claim 9 wherein the measuring step includes the step of inscribing a reference line along the Achilles' tendon portion of the person's foot.

11. A method of making a shoe correction for the alignment of a person's foot according to claim 10 wherein the measuring step further includes the step of measuring the lateral angular alignment of the reference line.

12. A method of making a shoe correction for the alignment of a person's foot according to claim 3 wherein the corrective components include supination, pronation, and arch control pads.

13. A method of making a shoe correction for the alignment of a person's foot according to claim 12 wherein the database further includes a correlation between lateral angular alignment values and an appropriate shoe type, and further comprising the step of selecting from the database an appropriate shoe type that correlates with the measured lateral angular alignment of the foot.

14. A method of making a shoe correction for the alignment of a person's foot according to claim 3 and further comprising the step of constructing a corrective alignment shoe by incorporating into the shoe the selected corrective components.

15. A method of making a shoe correction for the alignment of a person's foot according to claim 3 and further comprising the step of constructing a corrective alignment insole from a base insole and the selected corrective components.

16. A method of making a shoe correction for the alignment of a person's foot according to claim 2 and further comprising the step of constructing a corrective alignment shoe by incorporating into the shoe the selected corrective components.

17. A method of making a shoe correction for the alignment of a person's foot according to claim 2 and further comprising the step of constructing a corrective alignment insole from a base insole and the selected corrective components.

18. A method of making a shoe correction for the alignment of a person's foot according claim 17 and further comprising the step of incorporating the corrective alignment insole into the selected shoe type.

19. A method of making a shoe correction for the alignment of a person's foot according to claim 1 wherein the measuring step is carried out with the aid of a subtalar joint goniometer.

20. A method of making a shoe correction for the alignment of a person's foot according to claim 1 wherein the measuring step includes the step of inscribing a reference line along the Achilles' tendon portion of the person's foot.

21. A method of making a shoe correction for the alignment of a person's foot according to claim 20 wherein the measuring step further includes the step of measuring the lateral angular alignment of the reference line.

22. A kit for quantifying and making a shoe correction for a misalignment of a person's foot, comprising:
   a dorsiflexion template adapted to position the person's lower leg at a preselected forward angle with respect to an upper surface of the person's foot adjacent the ankle when the person is standing on the foot; and
   a subtalar joint inclinometer to measure the lateral angular alignment of the person's foot when the person's lower leg is inclined at the preselected angle.

23. A kit for quantifying and making a shoe correction for a misalignment of a person's foot according to claim 22 and further comprising at least one corrective alignment insole component.

24. A kit for quantifying and making a shoe correction for a misalignment of a person's foot according to claim 23 wherein the at least one corrective insole component comprises:
   a base insole in the general shape of a person's footprint having a lateral portion, a medial portion, and an arch stability portion;
   at least one supination control pad for adjusting the supination alignment of the person's foot;
   at least one pronation control pad for adjusting the pronation alignment of the person's foot; and
   at least one arch control pad for adjusting the support of the person's arch.

25. A kit for quantifying and making a shoe correction for a misalignment of a person's foot according to claim 24 and further comprising a database which correlates a range of lateral angular alignment values combinations with at least one of the corrective alignment insole components;
   wherein the at least one of the corrective alignment insole components can be selected from the database based upon the lateral angular alignment measurement obtained from the subtalar joint inclinometer.

26. A corrective alignment insole assembly for making a shoe correction for the alignment of a person's foot, comprising:
   a base insole in the general shape of a person's footprint having a lateral portion, a medial portion, and an arch stability portion, and adapted for correcting both pronation and supination in combination with at least one of at least one supination control pad, at least one pronation control pad, or at least one arch control pad;
   at least one supination control pad for adjusting the supination alignment of the person's foot;
   at least one pronation control pad for adjusting the pronation alignment of the person's foot; and
     at least one arch control pad for adjusting the support of the person's arch;
     wherein the at least one supination control pad, the at least one pronation control pad, and the at least one arch control pad are selected based upon a lateral angular alignment measurement of the person's foot.

27. The corrective alignment insole assembly of claim 25 wherein the base insole is divided into an irregularly-shaped supination control portion extending along the lateral portion of the base insole, an irregularly-shaped motion control portion extending along the medial portion of the base insole, and a crescent-shaped arch stability portion extending along the arch portion of the base insole.

28. The corrective alignment insole assembly of claim 27 wherein the at least one supination control pad comprises an irregularly-shaped member having a variable wedge-shaped cross section corresponding in size and shape to the supination control portion of the base insole, and having an anterior end, a posterior end, a medial edge, and a lateral edge, wherein the thickness of the at least one supination control pad decreases from the lateral edge to the medial edge, and from a portion along the lateral edge to the anterior end and the posterior end.

29. The corrective alignment insole assembly of claim 28 wherein the at least one supination control pad ranges in thickness from a maximum of 3/16 inch at the center lateral edge to 1/16 inch at the posterior end, to zero inches at the anterior end and along the medial edge.

30. The corrective alignment insole assembly of claim 29 wherein the at least one supination control pad comprises an irregularly-shaped supplementary supination control pad portion located at the center lateral portion of the at least one supination control pad.

31. The corrective alignment insole assembly of claim 30 wherein the at least one supination control pad comprises a supplementary supination control pad comprising an irregularly-shaped member having a generally wedge-shaped cross section corresponding in size and shape to the supplementary supination control pad portion, attached to the supination control pad at the supplementary supination control pad portion for increasing the maximum thickness of the supination control pad at its center lateral portion, and having an anterior end, a posterior end, a medial edge, and a lateral edge, wherein the thickness of the supination control pad decreases from the lateral edge to the medial edge, and from a portion along the lateral edge to the anterior end and the posterior end.

32. The corrective alignment insole assembly of claim 31 wherein the supplementary supination control pad varies in thickness from a maximum of ⅛ inch at the center lateral edge to zero inches at the anterior end, the posterior end, and the medial edge.

33. The corrective alignment insole assembly of claim 27 wherein the at least one motion control pad comprises an irregularly-shaped elongated member having a variable wedge-shaped cross section corresponding in size and shape to the motion control portion of the base insole, and having an anterior end, a posterior end, a medial edge, and a lateral edge, wherein the thickness of the at least one motion control pad decreases from the medial edge to the lateral edge, and from the portion along the medial edge to the anterior end and the posterior end.

34. The corrective alignment insole assembly of claim 33 wherein the at least one motion control pad ranges in thickness from a maximum of 3/16-inch along the anterior portion of the medial edge, to ⅛-inch at the posterior end, to zero inches at the anterior end and along the lateral edge.

35. The corrective alignment insole assembly of claim 34 wherein the at least one motion control pad comprises an irregularly-shaped supplementary motion control pad portion located at the anterior medial portion of the at least one motion control pad.

36. The corrective alignment insole assembly of claim 35 wherein the at least one motion control pad comprises a supplementary motion control pad comprising an irregularly-shaped member having a generally wedge-shaped cross-section corresponding in size and shape to the supplementary motion control pad portion, attached to the motion control pad at the supplementary motion control pad portion for increasing the maximum thickness of the motion control pad at its anterior medial portion, and having an anterior end, a posterior end, a medial edge, and a lateral edge, wherein the thickness of the at least one supplementary motion control pad decreases from the center medial edge to the anterior end, the posterior end, and the lateral edge.

37. The corrective alignment insole assembly of claim 36 wherein the supplementary motion control pad varies in thickness from a maximum of ⅛ inch at the center medial edge to zero inches at the anterior end, the posterior end, and the lateral edge.

38. The corrective alignment insole assembly of claim 27 wherein the at least one arch stability pad comprises a crescent-shaped member having a generally wedge-shaped cross section corresponding in size and shape to the arch stability portion of the base insole, and having an anterior end, a posterior end, a medial edge, and a lateral edge, wherein the thickness of the at least one arch stability pad decreases from the center medial edge to the lateral edge, the anterior end and the posterior end.

39. The corrective alignment insole assembly of claim 38 wherein the at least one arch stability pad ranges in thickness from a maximum of 3/16 inch at the center medial edge to zero inch from the anterior end along the lateral edge to the posterior end.

40. The corrective alignment insole assembly of claim 39 wherein the at least one arch stability pad comprises a supplementary arch stability pad comprising a crescent-shaped member having a generally wedge-shaped cross-section for attachment to the at least one arch stability pad for increasing the maximum thickness of the at least one arch stability pad at the arch stability portion of the base insole, and having an anterior end, a posterior end, a medial edge, and a lateral edge, wherein the thickness of the supplementary arch stability pad decreases from the center medial edge to the lateral edge, the anterior end, and the posterior end.

41. The corrective alignment insole assembly of claim 40 wherein the supplementary arch stability pad varies in thickness from a maximum of 3/16 inch at the center medial edge to zero inch from the anterior end along the lateral edge to the posterior end.

42. The corrective alignment insole assembly of claim 26 wherein the base insole further comprises a resilient heel cushioning zone for cushioning impact to the heel.

43. The corrective alignment insole assembly of claim 42 wherein the resilient heel cushioning zone comprises a pattern of cutout sections adapted to provide resilient cushioning immediately beneath the person's heel.

44. The corrective alignment insole assembly of claim 42 wherein the resilient heel cushioning zone comprises a low density gel pad adapted to provides resilient cushioning immediately beneath the person's heel.

45. The corrective alignment insole assembly of claim 44 wherein the low density gel pad comprises a low density gel polymer.

46. A subtalar joint inclinometer for measuring the lateral angular alignment of a person's foot when the person is in a standing position, comprising a calcaneal bisection gauge for inscribing reference line on the heel of the person aligned with the person's Achilles tendon and a protractor for determining the inclination of the reference line when the person is standing.

47. A subtalar joint inclinometer for measuring the lateral angular alignment of a person's foot when the person is in a standing position, comprising:
   a base having a first portion adapted to be positioned beneath the heel of a person in a standing position and a second portion orthogonal with respect to the first portion and adapted to be placed adjacent to the Achilles tendon of the person whose heel is positioned on the base first portion;
   a heel alignment member adapted to be positioned on the heel of the person whose heel is positioned on the base first portion; and
   a protractor scale indicia on one of the base second portion and the heel alignment member and a reference line indicia on the other of the base second portion and the heel alignment member, wherein the reference line indicia is aligned with a zero position on the protractor scale indicia when the person's heel has a zero angular alignment and is adapted to indicate on the protractor scale indicia the degree of angular deviation of the person's foot from zero angular alignment.

48. A subtalar joint inclinometer according to claim 47 wherein the heel alignment member is pivotally mounted to the base.

49. A subtalar joint inclinometer according to claim 47 wherein the heel alignment member has wings which are adapted to cradle the heel of the person whose heel is positioned on the base first portion.

50. A subtalar joint inclinometer according to claim 47 wherein the protractor scale indicia is disposed on the heel alignment member and the reference line indicia is disposed on the base second portion.

51. A database for selecting at least one corrective alignment insole component for making a shoe correction for a misalignment of a person's foot based upon a measurement of a lateral angular alignment of the person's foot, comprising:
   a plurality of preselected lateral angular alignment values; and
   at least one corrective alignment insole component comprising at least one of a base insole, a supination control pad, a supplementary supination control pad, a motion control pad, and a supplementary motion control pad;
   wherein a lateral angular alignment value of −5° to 3° correlates to an assembly of corrective alignment insole components comprising a base insole, a supination control pad, and a supplementary supination control pad.

52. A database for selecting at least one corrective alignment insole component for making a shoe correction for a misalignment of a person's foot based upon a measurement of a lateral angular alignment of the person's foot, comprising:
   a plurality of preselected lateral angular alignment values; and
   at least one corrective alignment insole component comprising at least one of a base insole, a supination control pad, a supplementary supination control pad, a motion control pad, and a supplementary motion control pad;
   wherein a lateral angular alignment value of 3° to 6° correlates to an assembly of corrective alignment insole components comprising a base insole, and a supination control pad.

53. A database for selecting at least one corrective alignment insole component for making a shoe correction for a misalignment of a person's foot based upon a measurement of a lateral angular alignment of the person's foot, comprising:
   a plurality of preselected lateral angular alignment values; and
   at least one corrective alignment insole component comprising at least one of a base insole, a supination control pad, a supplementary supination control pad, a motion control pad, and a supplementary motion control pad;
   wherein a lateral angular alignment value of 6° to 9° correlates to an assembly of corrective alignment insole components comprising a base insole.

54. A database for selecting at least one corrective alignment insole component for making a shoe correction for a misalignment of a person's foot based upon a measurement of a lateral angular alignment of the person's foot, comprising:
   a plurality of preselected lateral angular alignment values; and
   at least one corrective alignment insole component comprising at least one of a base insole, a supination control pad, a supplementary supination control pad, a motion control pad, and a supplementary motion control pad;
   wherein a lateral angular alignment value of 9° to 12° correlates to an assembly of corrective alignment insole components comprising a base insole, and a supplementary motion control pad.

55. A database for selecting at least one corrective alignment insole component for making a shoe correction for a misalignment of a person's foot based upon a measurement of a lateral angular alignment of the person's foot, comprising:
   a plurality of preselected lateral angular alignment values; and
   at least one corrective alignment insole component comprising at least one of a base insole, a supination control pad, a supplementary supination control pad, a motion control pad, and a supplementary motion control pad;
   wherein a lateral angular alignment value of 12° to 15° correlates to an assembly of corrective alignment insole components comprising a base insole, and a motion control pad.

56. A database for selecting at least one corrective alignment insole component for making a shoe correction for a misalignment of a person's foot based upon a measurement of a lateral angular alignment of the person's foot, comprising:
   a plurality of preselected lateral angular alignment values; and
   at least one corrective alignment insole component comprising at least one of a base insole, a supination control pad, a supplementary supination control pad, a motion control pad, and a supplementary motion control pad;
   wherein a lateral angular alignment value of greater than 15° correlates to an assembly of corrective alignment insole components comprising a base insole, a motion control pad, and a supplementary motion control pad.

57. The database according to any one of claim 50, 52, 53, 54, 55, or 56 wherein the database further includes a correlation between the plurality of lateral angular alignment values with a variety of shoe types and wherein the appropriate corrective shoe can be selected for use with the selected at least one corrective alignment insole component.

* * * * *

UNITED STATES PATENT AND TRADEMARK OFFICE
CERTIFICATE OF CORRECTION

PATENT NO. : 7,069,665 B1
APPLICATION NO. : 10/604418
DATED : July 4, 2006
INVENTOR(S) : Adriano Rosa It is certified that error appears in the above-identified patent and that said Letters Patent is hereby corrected as shown below:

In the Patent Header:

It reads: (12) United States Patent
 Adriano

It should read: (12) United States Patent
 Rosa

On the Front Page:

It reads: (75) Inventor: Rosa Adriano, Caledonia, MI (US)

It should read: (75) Inventor: Adriano Rosa, Caledonia, MI (US)

In the Claims:

Claim 44, Column 20, line 34, reads: "...gel pad adapted to provides resilient cushioning..."

It should read: "...gel pad adapted to provide resilient cushioning..."

Claim 46, Column 20, line 43, reads: "...for inscribing reference line on the heel..."

It should read: "...for inscribing a reference line on the heel..."

UNITED STATES PATENT AND TRADEMARK OFFICE
CERTIFICATE OF CORRECTION

PATENT NO. : 7,069,665 B1
APPLICATION NO. : 10/604418
DATED : July 4, 2006
INVENTOR(S) : Adriano Rosa It is certified that error appears in the above-identified patent and that said Letters Patent is hereby corrected as shown below:

Claim 57, Column 22, line 49, reads: "...according to any one of claim 50, 52, 53,"

It should read: "...according to any one of claims 50, 52, 53,"

Signed and Sealed this

Twelfth Day of September, 2006

JON W. DUDAS
*Director of the United States Patent and Trademark Office*